US009865119B2

(12) United States Patent
Isshiki et al.

(10) Patent No.: US 9,865,119 B2
(45) Date of Patent: Jan. 9, 2018

(54) PHARMACEUTICAL DISPENSING UNIT, PHARMACEUTICAL DISPENSING APPARATUS EQUIPPED WITH SAME, AND METHOD FOR CONTROLLING PHARMACEUTICAL DISPENSING APPARATUS

(71) Applicant: Panasonic Healthcare Holdings Co., Ltd., Tokyo (JP)

(72) Inventors: Taizo Isshiki, Ehime (JP); Hideyuki Morii, Ehime (JP); Keisuke Kita, Ehime (JP); Akiji Tanaka, Ehime (JP)

(73) Assignee: PANASONIC HEALTHCARE HOLDINGS CO., LTD., Tokyo (JP)

( * ) Notice: Subject to any disclaimer, the term of this patent is extended or adjusted under 35 U.S.C. 154(b) by 122 days.

(21) Appl. No.: 14/899,349

(22) PCT Filed: Aug. 1, 2014

(86) PCT No.: PCT/JP2014/004049
§ 371 (c)(1),
(2) Date: Dec. 17, 2015

(87) PCT Pub. No.: WO2015/033517
PCT Pub. Date: Mar. 12, 2015

(65) Prior Publication Data
US 2016/0133084 A1    May 12, 2016

(30) Foreign Application Priority Data

Sep. 5, 2013 (JP) ................................ 2013-183820
Sep. 5, 2013 (JP) ................................ 2013-183823

(51) Int. Cl.
G06F 7/00       (2006.01)
G07F 17/00      (2006.01)
(Continued)

(52) U.S. Cl.
CPC ......... *G07F 17/0092* (2013.01); *G05B 15/02* (2013.01); *G06F 19/3462* (2013.01); *G07G 1/0045* (2013.01)

(58) Field of Classification Search
None
See application file for complete search history.

(56) References Cited

U.S. PATENT DOCUMENTS 7,685,026 B1 *   3/2010   McGrady .............. G06F 19/327
                                                            705/2

FOREIGN PATENT DOCUMENTS

JP         7-8537       1/1995
JP      2005-125013     5/2005
(Continued)

OTHER PUBLICATIONS

International Search Report dated Nov. 4, 2014 in International (PCT) Application No. PCT/JP2014/004049.

*Primary Examiner* — Yolanda R Cumbess
(74) *Attorney, Agent, or Firm* — Wenderoth, Lind & Ponack, L.L.P.

(57) ABSTRACT

A removal head with improved performance in terms of reading pharmaceutical information. The removal head of the present invention comprises a movement path component, a first braking component, and a sensor. The movement path component moves a substantially cylindrical pharmaceutical container that has an identification label and that has been taken out of a pharmaceutical container holding cassette that holds pharmaceutical containers. The first braking component is provided to the end of the movement path component, and stops the pharmaceutical container that has moved along the movement path component at a specific location. The sensor reads the identification label of the pharmaceutical container whose movement has been stopped at a specific location by the braking component. The (Continued)

movement path component has a movement face that moves along the movement path of the pharmaceutical container, and the movement face has a contact component that comes into contact with the pharmaceutical container.

19 Claims, 20 Drawing Sheets

(51) Int. Cl.
    *G07G 1/00*         (2006.01)
    *G05B 15/02*       (2006.01)
    *G06F 19/00*       (2011.01)

(56) References Cited

FOREIGN PATENT DOCUMENTS

| | | | |
|---|---|---|---|
| JP | 2005125013 A | * | 5/2005 |
| JP | 2005-237713 | | 9/2005 |

* cited by examiner

PHARMACEUTICAL DISPENSING UNIT, PHARMACEUTICAL DISPENSING APPARATUS EQUIPPED WITH SAME, AND METHOD FOR CONTROLLING PHARMACEUTICAL DISPENSING APPARATUS

TECHNICAL FIELD

The present invention relates to a pharmaceutical dispensing unit that is used to improve efficiency in hospital work, for example, and to a pharmaceutical dispensing apparatus equipped with this unit.

BACKGROUND ART

Conventional pharmaceutical dispensing apparatuses equipped with a pharmaceutical dispensing unit of this type were configured to comprise a cassette in which cylindrical pharmaceutical containers were disposed, a container removal head for removing the pharmaceutical containers from this cassette, a holding means for holding the pharmaceutical containers taken out by this container removal head, and a reading device for reading pharmaceutical information attached to the pharmaceutical container (the following Patent Literature 1 is prior art that is similar to this).

CITATION LIST

Patent Literature

Patent Literature 1: Japanese Laid-Open Patent Application 2005-125013

SUMMARY

With the above-mentioned prior art, even though a reading device was provided for reading pharmaceutical information on the pharmaceutical container, there were situations in which the pharmaceutical information could not be properly read.

Specifically, when pharmaceutical information is read from a pharmaceutical container, the pharmaceutical container is rotated so that an identification label indicating the pharmaceutical information will face the sensing face of the reading device, but pharmaceutical containers come in a wide variety of shapes, not a few of which can be difficult to rotate. For instance, the cross section of a pharmaceutical container along its short side may be substantially elliptical, or the shape may be such that a thin line of molding material sticks out along substantially the entire length (in the lengthwise direction) around the outside of the pharmaceutical container.

Accordingly, the pharmaceutical container will not rotate smoothly even if an attempt is made to rotate it so that the identification label indicating pharmaceutical information that has been attached to the outer peripheral face of the pharmaceutical container will be pointed toward the sensing face, so the identification label will not necessarily be facing the sensing face of the reading device.

As a result, the reading device may not be able to accurately recognize the identification label, and may not be able to properly read the pharmaceutical information on the pharmaceutical container, so the desired level of reliability cannot be ensured.

In view of this, and in light of the above-mentioned problems encountered with conventional pharmaceutical dispensing units, it is an object of the present invention to provide a pharmaceutical dispensing unit with improved performance in terms of reading pharmaceutical information, as well as a pharmaceutical dispensing apparatus equipped with this unit, and a method for controlling a pharmaceutical dispensing apparatus.

To achieve this object, the pharmaceutical dispensing unit of the present invention comprises a movement path component, a first braking component, and a sensor. The movement path component moves a substantially cylindrical pharmaceutical container that has a first identification label and has been taken out of a cassette in which the pharmaceutical container is housed. The first braking component is provided to the end of the movement path component and stops the pharmaceutical container that has come along the movement path component at a specific location. The sensor reads the first identification label on the pharmaceutical container whose movement has been stopped at the specific location by the first braking component. The movement path component has a first movement face that moves along the movement path of the pharmaceutical container. The first movement face has a first contact component that comes into contact with the pharmaceutical container.

The present invention provides a pharmaceutical dispensing unit with improved performance in terms of reading pharmaceutical information, as well as a pharmaceutical dispensing apparatus equipped with this unit, and a method for controlling a pharmaceutical dispensing apparatus.

DESCRIPTION OF EMBODIMENTS

Embodiments of the present invention will now be described through reference to the drawings.

Embodiment 1

1. Configuration

Overview of Pharmaceutical Dispensing Apparatus

Figure 1:
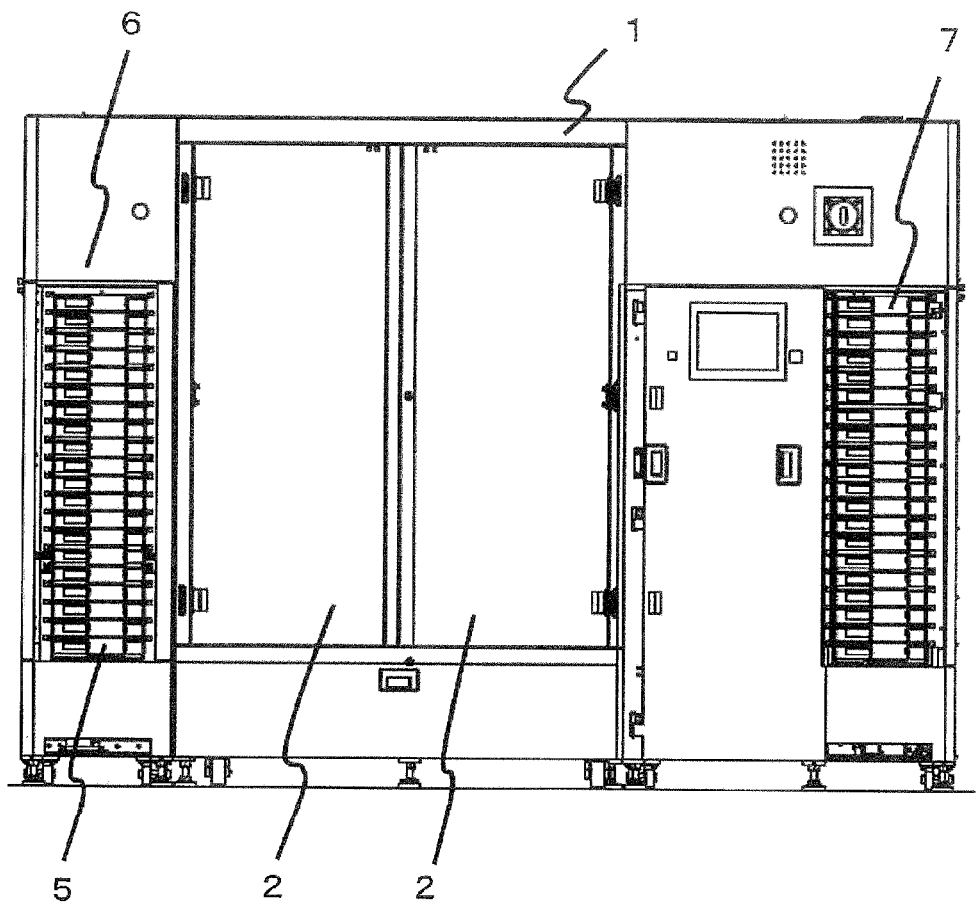
FIG. 1 is a front view of a pharmaceutical dispensing apparatus equipped with a removal head pertaining to Embodiment 1 of the present invention.

FIG. 1 is an example of a pharmaceutical dispensing apparatus, and is a front view of a pharmaceutical dispensing apparatus equipped with the pharmaceutical dispensing unit pertaining to Embodiment 1 in the present invention.

Figure 2:
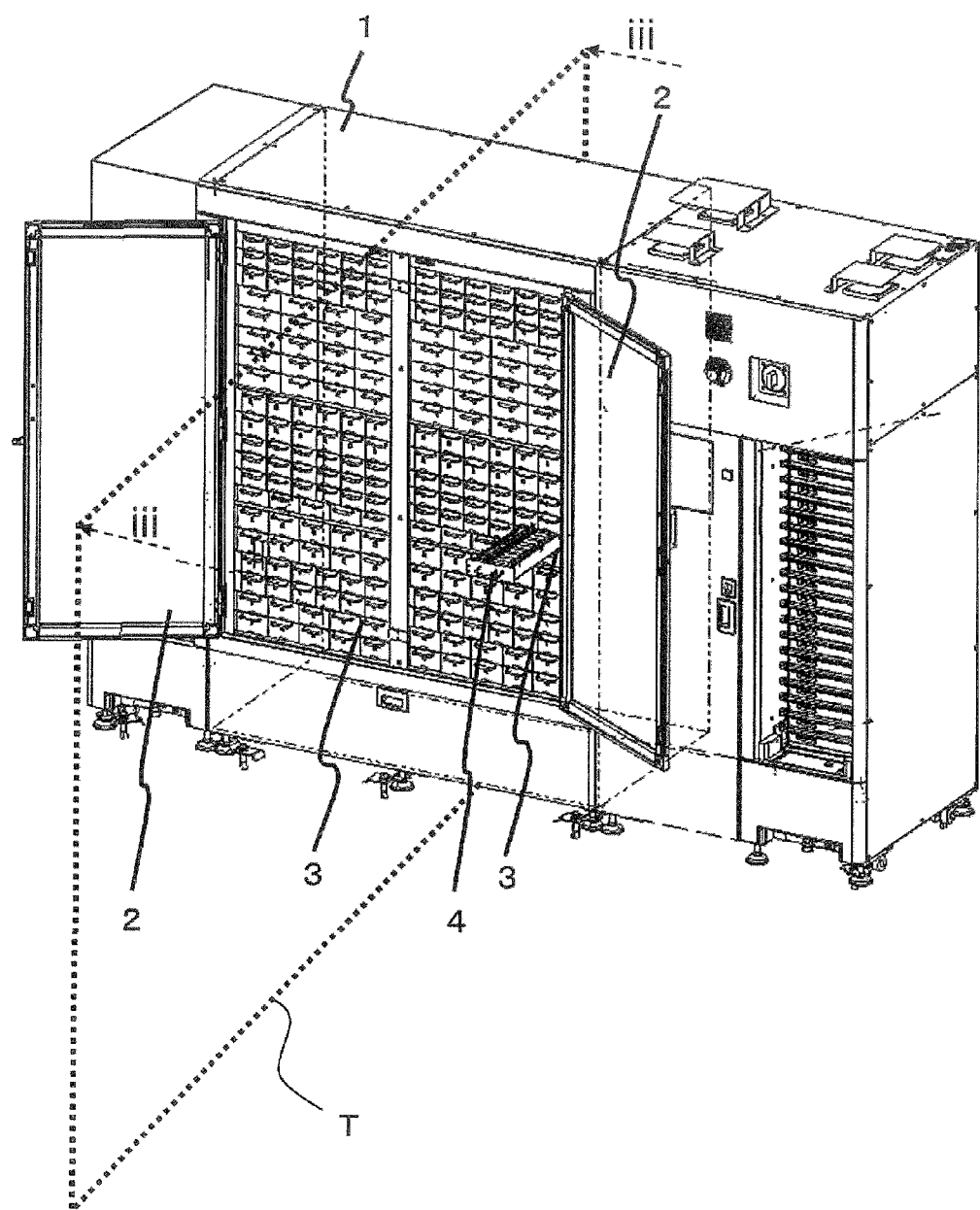
FIG. 2 is an oblique view of the pharmaceutical dispensing apparatus pertaining to Embodiment 1 of the present invention.

In FIG. 1, 1 is the main cabinet of the pharmaceutical dispensing apparatus. When the front doors 2 of this cabinet are opened as shown in FIG. 2, it is revealed that a plurality of cassette mounting slots 3 are provided in this portion. Pharmaceutical container holding cassettes 4 are mounted in these cassette mounting slots 3.

As shown in FIG. 1, a storage compartment 6 for storing empty trays 5 used to dispense pharmaceutical containers is provided on the left side of the main cabinet 1 of the pharmaceutical dispensing apparatus. A storage compartment 7 for storing trays 5 containing dispensed pharmaceutical containers is provided on the right side of the main cabinet 1.

That is, the trays 5 stored in the storage compartment 6 are transferred to the lower part of the cassette mounting slots 3, where pharmaceutical containers held in the pharmaceutical container holding cassettes 4 are put on the trays. The trays holding the pharmaceutical containers are then stored in the storage compartment 7 as shown in FIG. 1.

Figure 3:
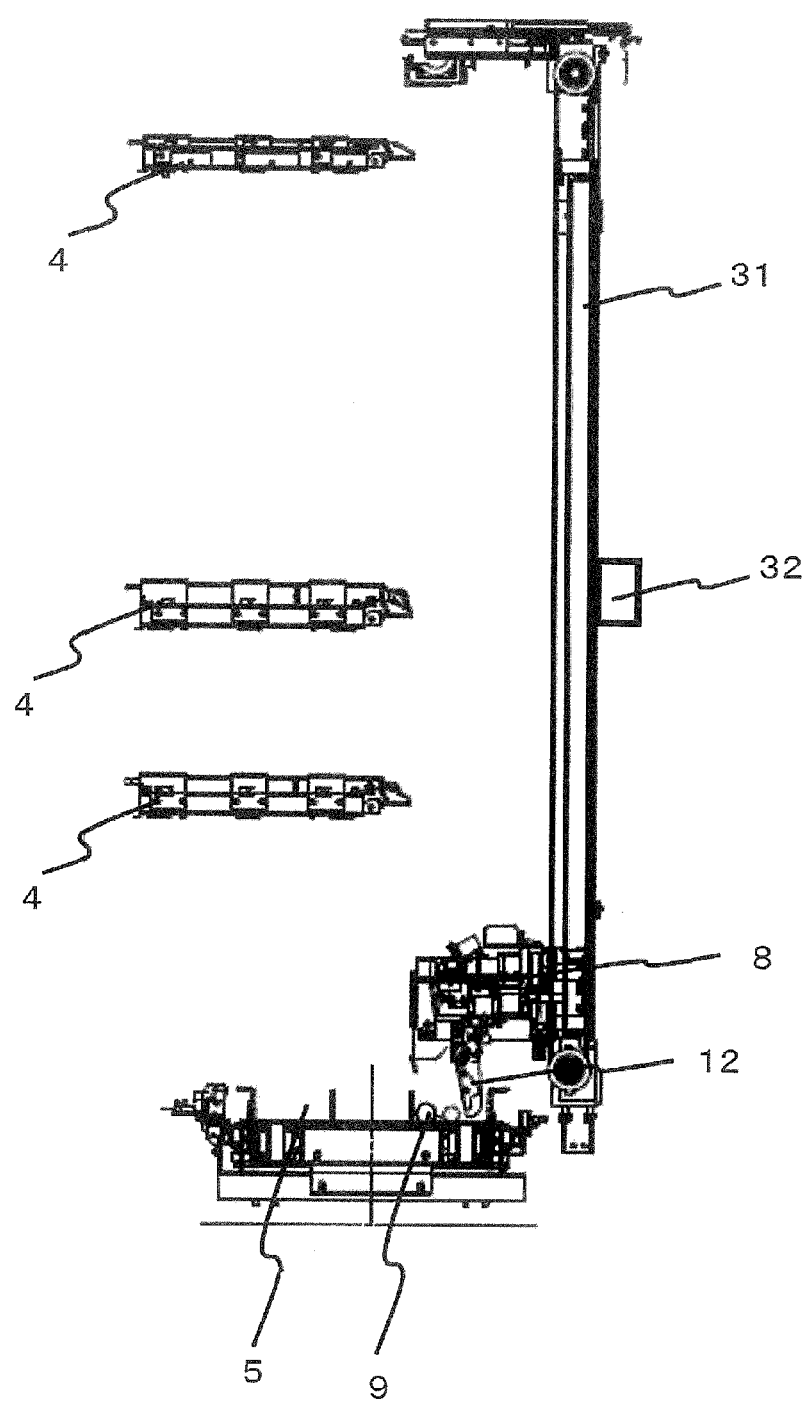
FIG. 3 is a cross section of the main portions of the removal head as seen in the iii-iii direction in the cross section T of FIG. 2.

More specifically, as shown in FIG. 3, a tray 5 is transferred to the lower part of the cassette mounting slots 3 as discussed above, and the system goes into a standby state. In this state, a removal head 8 (an example of a pharmaceutical dispensing unit) moves to the rear face side of the pharmaceutical container holding cassette 4 containing a pharmaceutical container of the pharmaceutical indicated by prescription, and the pharmaceutical container 9 removed by the removal head 8 is loaded onto the tray 5 by this removal head 8 dropping.

FIG. 3 is a cross section of the main portion of the pharmaceutical dispensing unit as seen in the arrow iii direction in the T cross section in FIG. 2. A T cross section shows a plane parallel to the depth direction of the pharmaceutical dispensing apparatus (from the front face side to the rear face side), and is a plane that is perpendicular to the ground. The arrow iii indicates a direction perpendicular to the T cross section.

Removal Head 8

Figure 4:
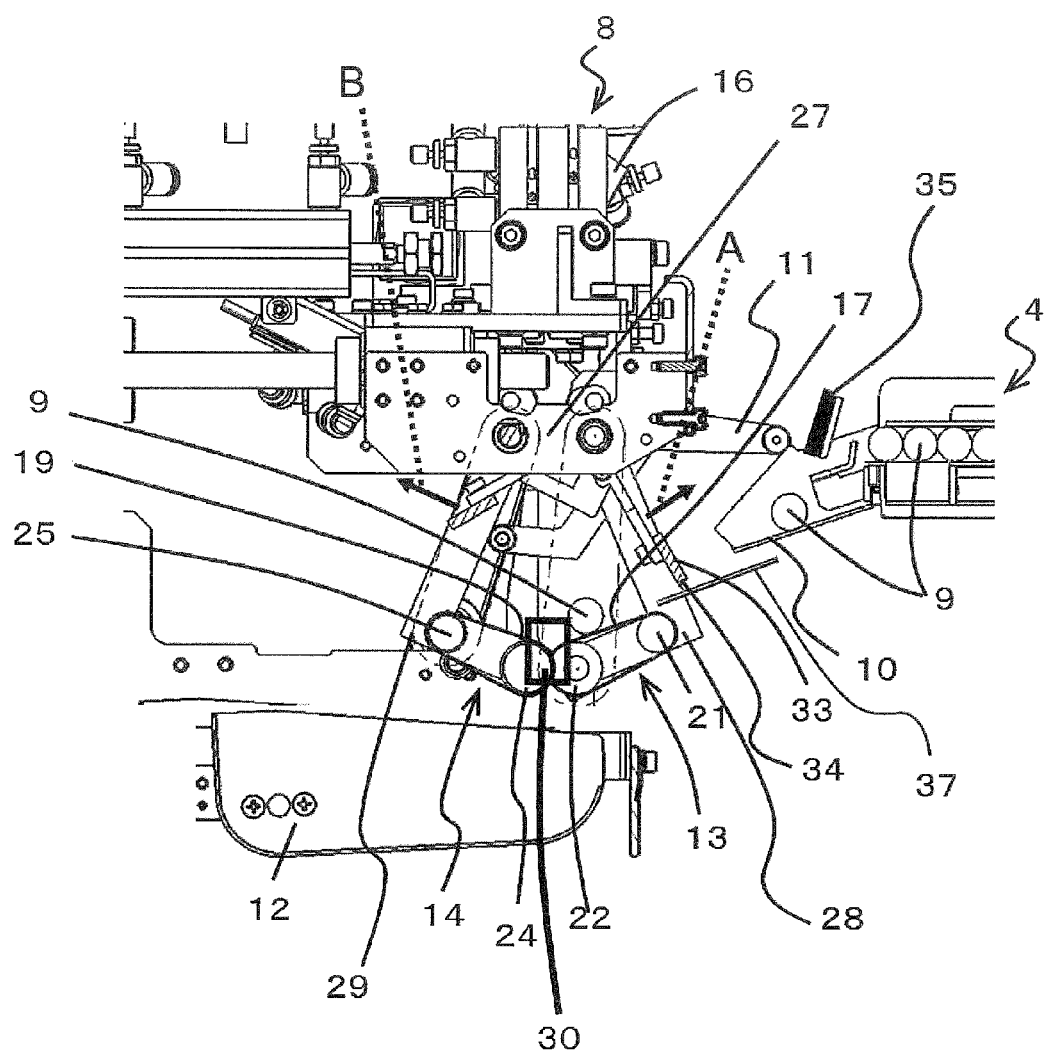
FIG. 4 illustrates the main parts of the removal head in the pharmaceutical dispensing apparatus pertaining to Embodiment 1 of the present invention.

FIG. 4 is a diagram of the portion where the pharmaceutical containers 9 are removed by the removal head 8 in this embodiment.

The configuration of this removal portion is well know, and therefore will be described only briefly to avoid making the description too complicated.

When a removal lever 10 on a pharmaceutical container holding cassette 4 is operated by an operating component 11 of the removal head 8, the pharmaceutical container 9 held in the pharmaceutical container holding cassette 4 is taken out of the pharmaceutical container holding cassette 4 as shown in FIG. 4, and rolls down toward a holding pocket 12 (an example of a holding component) provided at the lower part of the removal head 8.

After it finishes rolling, the pharmaceutical container 9 is temporarily stored in the holding pocket 12, and then it is moved from the holding pocket 12 onto a tray 5 standing by under the removal head 8 as shown in FIG. 3.

The removal head 8 in this embodiment reads the pharmaceutical information on the pharmaceutical container 9 in between from the chemical container 9 is removed from the pharmaceutical container holding cassette 4 as discussed above to the chemical container 9 is stored in the holding pocket 12.

Figure 5:
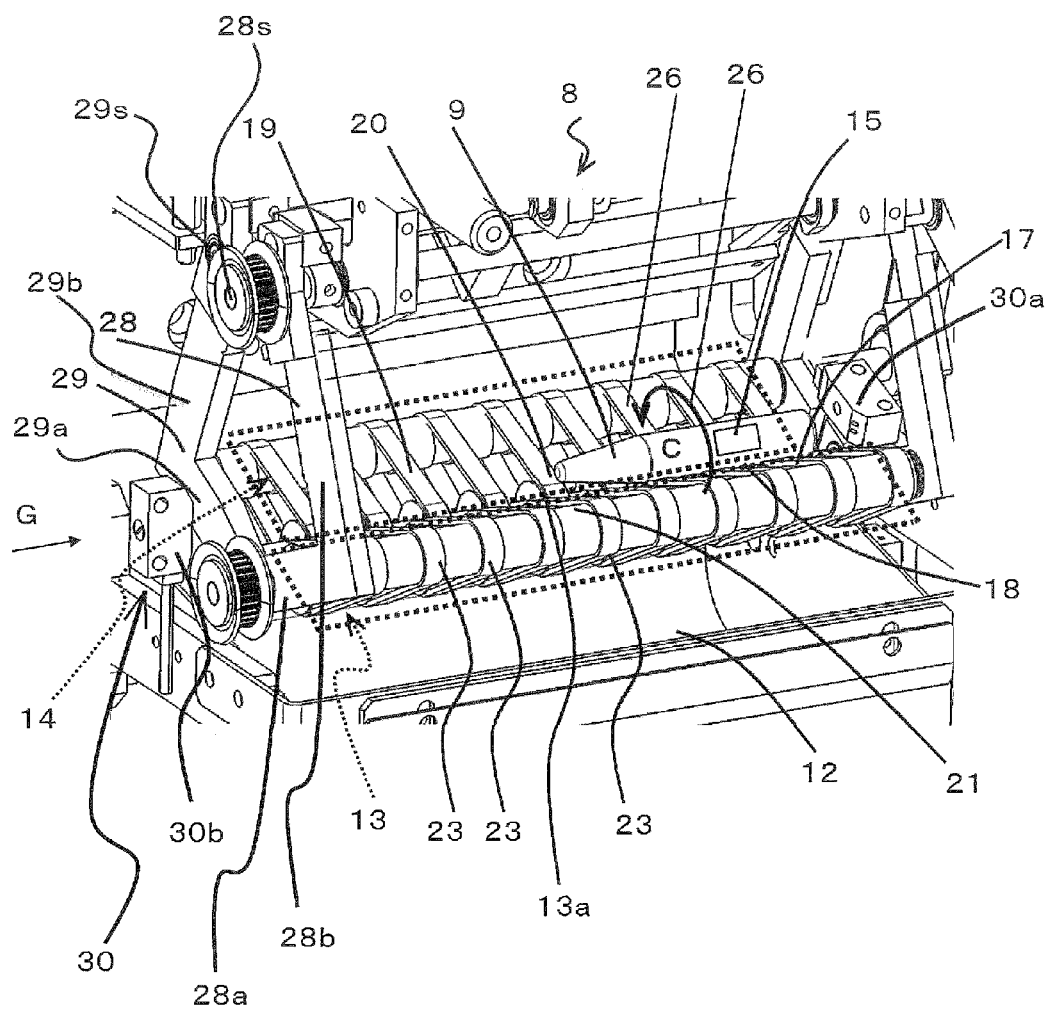
FIG. 5 illustrates the main parts of the removal head in the pharmaceutical dispensing apparatus pertaining to Embodiment 1 of the present invention.

Specifically, as shown in FIGS. 4 and 5, the removal head 8 in this embodiment comprises a movement path component 13 that moves the pharmaceutical container 9 toward the holding pocket 12, a first braking component 14 (an example of a first braking component) that is provided to the end of the movement path component 13 to stop the pharmaceutical container 9 that has moved along this movement path component 13 at a specific location, and a sensor 16 that reads an identification label 15 (an example of a first identification label) on the pharmaceutical container 9 whose movement has been stopped at the specific location by the first braking component 14.

Pharmaceutical Container 9

Figure 6:
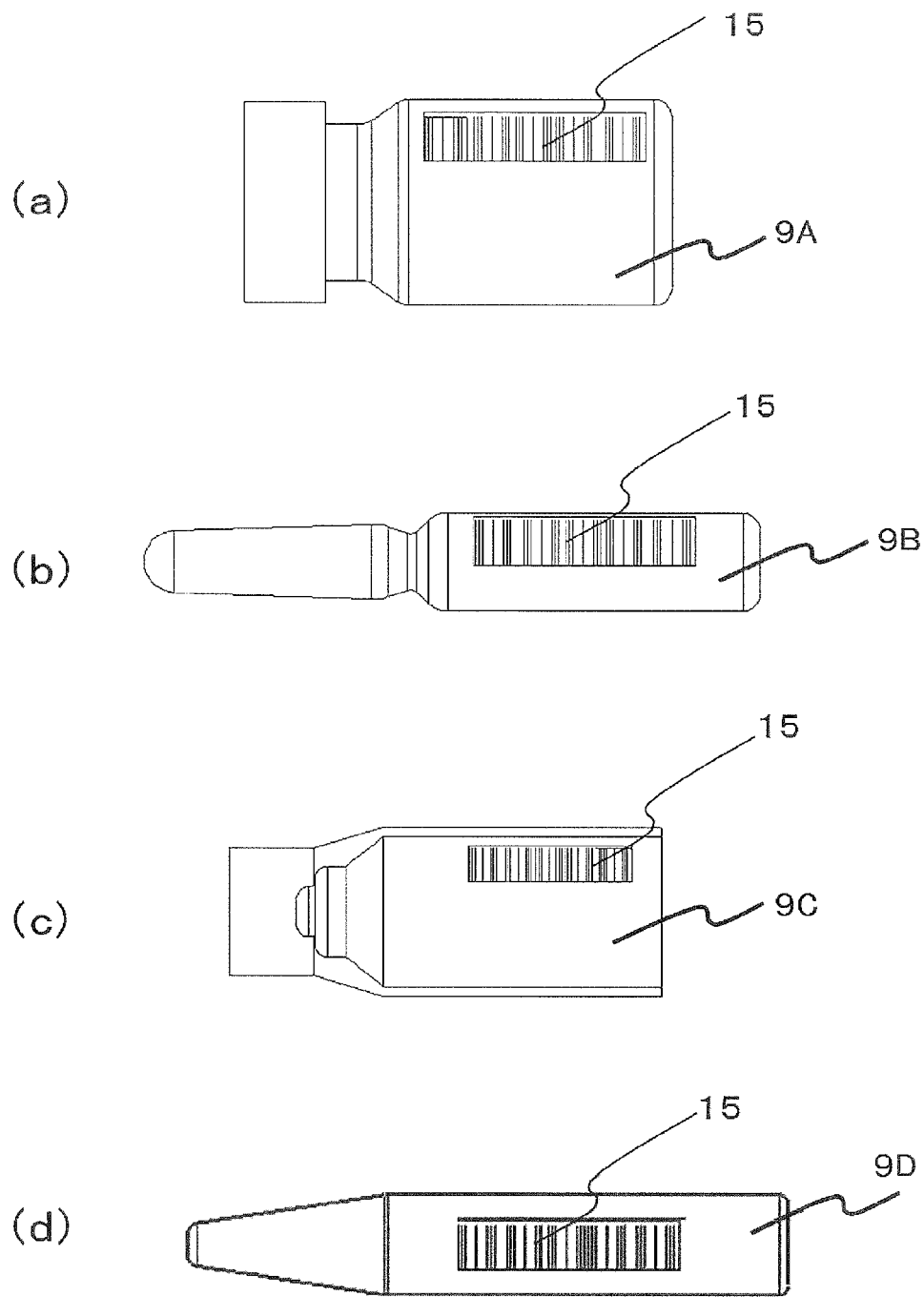
FIG. 6 consists of side views of the pharmaceutical container pertaining to Embodiment 1 of the present invention, with FIG. 6a being a side view of a pharmaceutical container 9A, FIG. 6b a side view of a pharmaceutical container 9B, FIG. 6c a side view of a pharmaceutical container 9C, and FIG. 6d a side view of a pharmaceutical container 9D.

As shown in FIG. 6, the pharmaceutical container 9 can be any of a wide variety of containers of various shapes, sizes, and so forth, as indicated by the pharmaceutical container 9A, the pharmaceutical container 9B, the pharmaceutical container 9C, and the pharmaceutical container 9D, and has a substantially cylindrical shape formed by molding a plastic, glass, or the like.

Specific pharmaceuticals are contained in the pharmaceutical containers 9, and as shown in FIG. 6, identification labels 15, which indicate pharmaceutical information about the pharmaceuticals contained in the pharmaceutical containers 9 (9A, 9B, 9C, and 9D in FIG. 6), are attached to the outer peripheral faces of the pharmaceutical containers 9 (9A, 9B, 9C, and 9D in FIG. 6).

The identification labels 15 are provided by printing or otherwise applying a barcode or other such identification means, for example, and are affixed with an adhesive agent or the like to the pharmaceutical containers 9, for example.

Overview of Movement Path Component 13

As shown in FIGS. 4 and 5, the movement path component 13 has a movement face 17 (an example of a first movement face) that moves along the movement path of the pharmaceutical containers 9. This movement face 17 comprises a contact component 18 (an example of a first contact component) that comes into contact with the pharmaceutical container 9 as shown in FIG. 5.

When a pharmaceutical container 9 has been taken out of a pharmaceutical container holding cassette 4, it moves toward the holding pocket 12 while rolling over the movement face 17 of the movement path component 13.

The configuration may also be such that the movement face 17 moves in the opposite direction from the movement direction of the pharmaceutical containers 9.

Specifically, the configuration is such that when a pharmaceutical container 9 that has been taken out of a pharmaceutical container holding cassette 4 moves toward the holding pocket 12 while rolling over the movement face 17 of the movement path component 13, the pharmaceutical container 9 is subjected to a force in the opposite direction from the movement direction of the pharmaceutical container 9. This reduces the movement speed of the pharmaceutical container 9. Here, the rotational direction of the pharmaceutical container 9 is counter-clockwise as seen from the arrow G direction in the state shown in FIG. 5, and is indicated by the arrow C in FIG. 5.

Overview of First Braking Component 14

As shown in FIG. 5, the first braking component 14 has a movement face 19 (an example of a second movement face) that moves in the opposite direction from the movement direction of the pharmaceutical container 9. This movement face 19 comprises a contact component 20 (an example of a second contact component) that comes into contact with the pharmaceutical container 9.

Specifically, the movement of the pharmaceutical container 9 that is moving toward the holding pocket 12 while rolling over the movement face 17 of the movement path component 13 is stopped at the location where the pharmaceutical container 9 comes into contact with the contact component 20 of the movement face 19.

That is, the configuration is such that when the pharmaceutical container 9 is moving toward the holding pocket 12 while rolling over the movement face 17 of the movement path component 13, the pharmaceutical container 9 is subjected to a force in the opposite direction from the movement direction of the pharmaceutical container 9. This stops the movement speed of the pharmaceutical container 9. Here, the rotational direction of the pharmaceutical container 9 is counter-clockwise as seen from the arrow G direction in the state shown in FIG. 5, and is indicated by the arrow C in FIG. 5.

Detailed Configuration of Movement Path Component 13

More precisely, the movement path component 13 is configured as follows.

A roller 21 (an example of a first roller) is provided on the pharmaceutical container holding cassette 4 side, in between the pharmaceutical container holding cassette 4 and the first braking component 14, and a roller 22 (an example of a second roller) is provided more toward the first braking component 14 side than the roller 21. This roller 22 is positioned lower than the roller 21. That is, as shown in FIG. 4, the roller 22 is disposed closer to the holding pocket 12 than the roller 21.

As shown in FIG. 5, first belts 23 go between the roller 21 and the roller 22. That is, the first belts 23 that go between the roller 21 and the roller 22 form an inclined face that rises up to the right on the upper side of the roller 21 and the roller 22 as shown in FIG. 4. With the movement path component 13 configured in this way, at least one of the roller 21 and the roller 22 is rotationally driven, which causes the first belts 23 to rotate between the roller 21 and the roller 22. In this embodiment, the roller 22 is rotated clockwise, for example, which causes the first belts 23 that go between the roller 21 and the roller 22 to rotate clockwise (see the arrow D in FIG. 7; discussed below).

As shown in FIG. 4, the movement face 17 is formed by moving the inclined face that rises to the right and is formed on the upper side of the roller 21 and the roller 22, upward and to the right.

Detailed Configuration of First Braking Component 14

Furthermore, in this embodiment, the first braking component 14 is configured as follows.

As shown in FIG. 4, a roller 24 (an example of a third roller) is provided to the rear of the movement face 17 in the movement direction of the pharmaceutical container 9, and a roller 25 (an example of a fourth roller) is provided to the rear of this roller 24. The roller 25 is disposed above the roller 24. That is, as shown in FIG. 4, the roller 25 is disposed farther away from the holding pocket 12 than the roller 24.

As shown in FIG. 5, second belts 26 go between the roller 24 and the roller 25. That is, the second belts 26 that go between the roller 24 and the roller 25 form an inclined face that descends to the right on the upper side of the roller 24 and the roller 25 as shown in FIG. 4.

With the first braking component 14 thus configured, at least one of the roller 24 and the roller 25 is rotationally driven to rotate the second belts 26 between the roller 24 and the roller 25. In this embodiment, for example, the roller 24 is rotated clockwise, and the second belts 26 that go between the roller 24 and the roller 25 are also rotated clockwise (see the arrow E in FIG. 7, discussed below).

As shown in FIG. 4, the inclined face that slopes down to the right and is formed on the upper side of the roller 24 and the roller 25 is moved downward and to the right to form the movement face 19.

Layout Relation Between Movement Path Component 13 and First Braking Component 14

Figure 7:
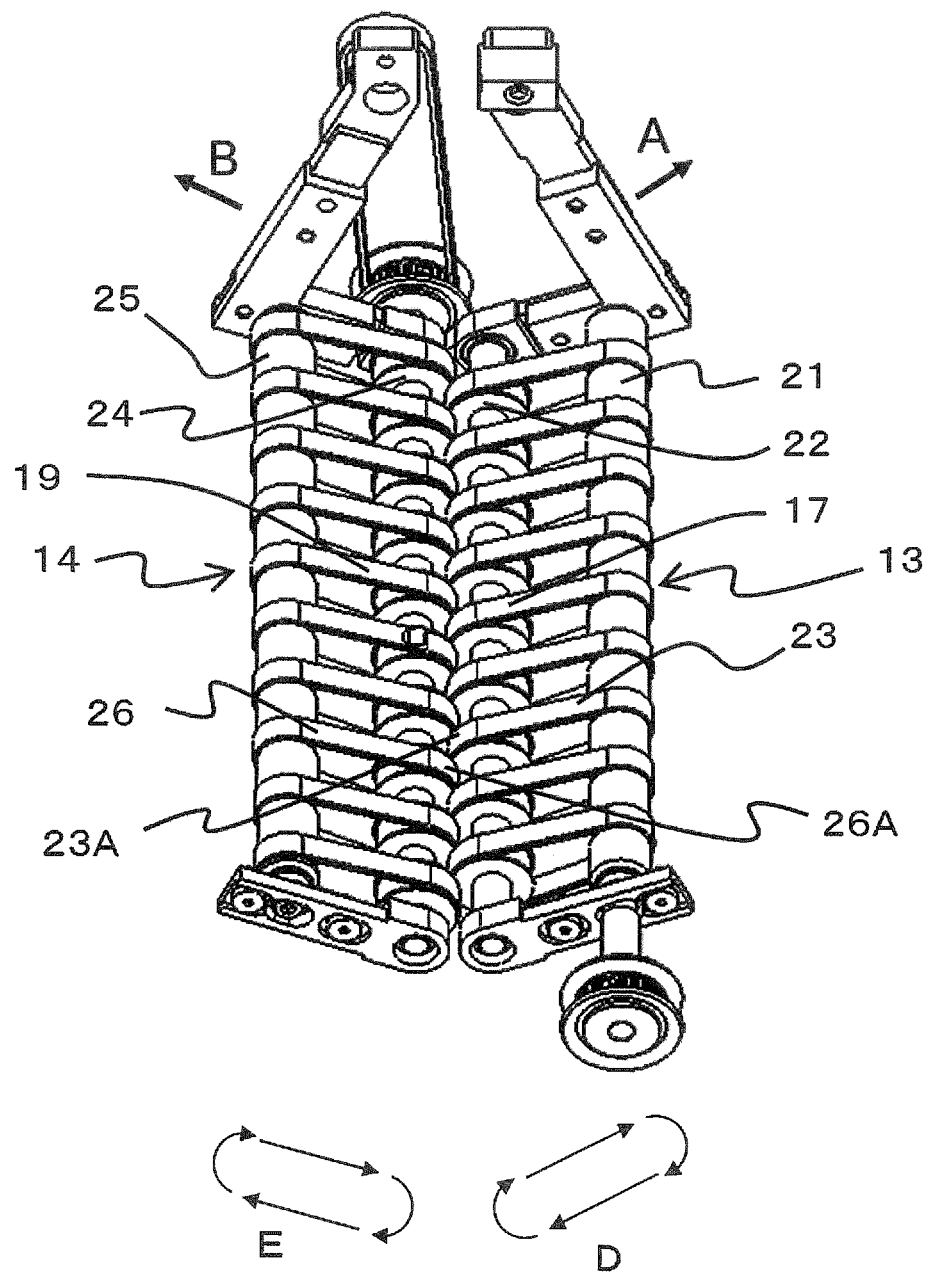
FIG. 7 illustrates the main parts of the removal head in the pharmaceutical dispensing apparatus pertaining to Embodiment 1 of the present invention.

Next, the layout relation between the first belts 23 and the second belts 26 will be described. FIG. 7 is an oblique view of the movement path component 13 and the first braking component 14 as seen from above.

As shown in FIG. 7, a plurality of the first belts 23 are provided, and these first belts 23 are wound between the roller 21 and the roller 22 at a specific spacing. A plurality of the second belts 26 are provided, and these second belts 26 are wound between the roller 24 and the roller 25 at a specific spacing.

Furthermore, as shown in FIG. 7, the ends 23A of the first belts 23 are disposed in the specific gaps between the second belts 26, and the ends 26A of the second belts 26 are disposed in the specific gaps between the first belts 23. The configuration is thus such that the ends 23A of the first belts 23 and the ends 26A of the second belts 26 intersect in the movement direction of the pharmaceutical container 9. In other words, it can be said that the ends 23A and the ends 26A are disposed alternating in the direction perpendicular to the movement direction.

With this configuration, part of the outer peripheral part of the pharmaceutical container 9 can reliably be in contact with at least one of the first belts 23 and the second belts 26 even with a shape having a thin protrusion in the lengthwise direction at the outer peripheral part of the pharmaceutical container 9, for example. Therefore, the pharmaceutical container 9 can be rotated more reliably, the identification label 15 of the pharmaceutical container 9 can be pointed in the direction of the sensor 16, and the identification label 15 of the pharmaceutical container 9 can be read more reliably by the sensor 16.

Here, at least one of the first belts 23 and the second belts 26 may be rubber belts. Using rubber belts raises the coefficient of friction between the pharmaceutical container 9 and the belts, so the pharmaceutical container 9 can be rotated more reliably.

Driver 27, Arm 28, and Arm 29

As shown in FIG. 4, the removal head 8 also comprises a driver 27. The driver 27 is configured so that an arm 28 (an example of a first arm) connected to the movement path component 13 can be driven in the direction of the arrow A shown in FIG. 4. More precisely, as shown in FIG. 5, the arm 28 is an L-shaped member and has a first member 28a and a second member 28b. The first member 28a is disposed along the movement path component 13, and to the side of the movement path component 13, and is fixed to the movement path component 13. The second member 28b is disposed so as to extend from the end of the first member 28a on the roller 21 side toward the driver 27. The driver 27 is constituted by a motor, a gear, etc., for example, and is linked to the second member 28b and rotates the second member 28b around a rotational shaft 28s at the upper end thereof. When the second member 28b is rotated in the arrow A direction, the movement path component 13 fixed to the first member 28a also moves in the arrow A direction.

Furthermore, the driver 27 is configured so that an arm 29 (an example of a second arm) connected to the first braking component 14 can be driven in the direction of the arrow B shown in FIG. 4. More precisely, as shown in FIG. 5, the arm 29 is an L-shaped member and has a first member 29a and a second member 29b. The first member 29a is disposed along the first braking component 14, and to the side of the first braking component 14, and is fixed to the first braking component 14. The second member 29b is disposed so as to extend from the end of the first member 29a on the roller 25 side toward the driver 27. The second member 29b is linked to the driver 27, and the driver 27 rotates the second member 29b around a rotational shaft 29s at the upper end thereof. When the second member 29b rotates in the arrow B direction, the first braking component 14 fixed to the first member 29a also rotates in the arrow B direction.

That is, the removal head 8 is configured so that the space between the movement path component 13 and the first braking component 14 can be opened and closed by the driver 27.

In this embodiment, it was described that the arm 28 connected to the movement path component 13 and the arm 29 connected to the first braking component 14 are both driven to open and close the space between the movement path component 13 and the first braking component 14, but just the movement path component 13 or the first braking component 14 may be moved to open and close the space between the movement path component 13 and the first braking component 14.

Container Detector 30 and Vibrator 32

Figure 8:
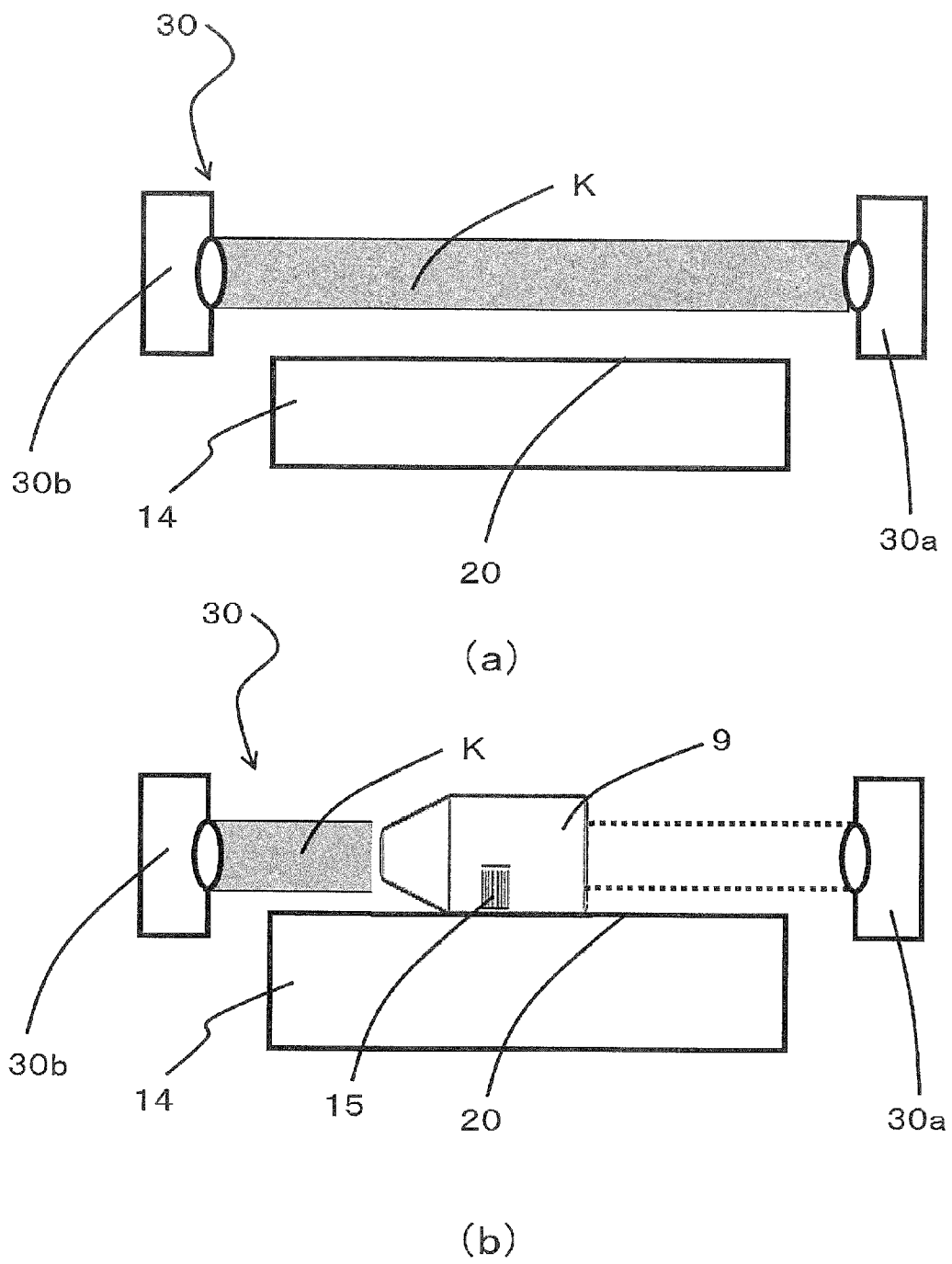
FIG. 8 consists of simplified diagrams illustrating the operation of the container detector pertaining to Embodiment 1 of the present invention, with FIG. 8a being a concept diagram of when there is no pharmaceutical container in a container detection region K, and FIG. 8b a concept diagram of when there is a pharmaceutical container in the container detection region K.

As shown in FIG. 5, the removal head 8 also comprises a container detector 30. FIGS. 8a and 8b are schematic diagrams of the configuration of the container detector 30. In this embodiment, a transmission type of opto-electric sensor is used, for example, as the container detector 30, and the container detector 30 has a light projector 30a that emits light and a light receiver 30b that receives light from the light projector 30a. The container detector 30 is disposed so that a container detection region K of the container detector 30 (the region between the light projector 30a and the light receiver 30b) is over the contact component 20 of the first braking component 14 (see FIG. 8a). When the pharmaceutical container 9 is within the container detection region K, as shown in FIG. 8b, light from the light projector 30a is blocked, so the presence of the pharmaceutical container 9 can be detected.

Therefore, the container detector 30 can confirm whether or not the pharmaceutical container 9 is on the contact component 20.

As shown in FIG. 3, the pharmaceutical dispensing apparatus of the present invention comprises the vibrator 32, which is provided to a removal head movement component 31 that moves the removal head 8.

If the container detector 30 detects the pharmaceutical container 9, that is, if the container detector 30 confirms that the pharmaceutical container 9 is present in the gap portion between the movement path component 13 and the first braking component 14, the pharmaceutical dispensing apparatus of this embodiment vibrates the vibrator 32 provided to the removal head movement component 31 that moves the removal head 8, and vibrates the entire removal head 8.

Thus vibrating the vibrator 32 and vibrating the entire removal head 8 allows the pharmaceutical container 9 that was standing up in the holding pocket 12 to be laid down on its side in the holding pocket 12. Specifically, the pharmaceutical container 9 can be put in a state in which it will pass more reliably through the gap between the movement path component 13 and the first braking component 14.

Second Braking Component 33

As shown in FIG. 4, the pharmaceutical dispensing apparatus in this embodiment also comprises a second braking component 33 (an example of a second braking component).

That is, the pharmaceutical dispensing apparatus in this embodiment is configured to further comprise the second braking component 33, which temporarily stops the movement of the pharmaceutical container 9 at a specific location between the first braking component 14 and the pharmaceutical container holding cassette 4.

Figure 9A:
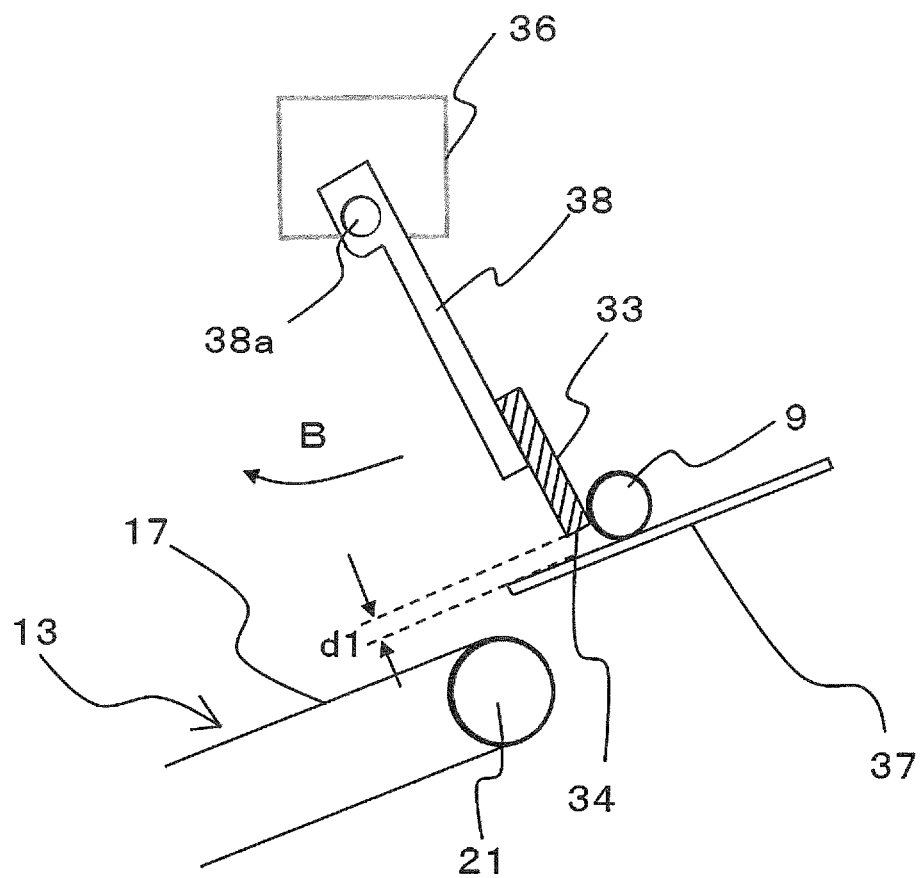
FIG. 9A is a schematic diagram of the area near a second braking component of the removal head in Embodiment 1 of the present invention.

The second braking component 33 is formed by a flat elastic body, for example, and as shown in FIG. 4, the lower end 34 is located near the upper face of a guide path 37 disposed between the removal lever 10 and the movement path component 13. FIG. 9A is a simplified detail view of the area near the second braking component 33. As shown in FIG. 9A, the gap d1 between the upper face of the guide path 37 and the end 34 of the second braking component 33 should be less than half the diameter of the pharmaceutical container 9, for example. This allows the movement of the pharmaceutical container 9 to the movement path component 13 to be stopped.

The second braking component 33 is configured so that the end 34 is moved away from the guide path 37 by a braking driver 36 (an example of a second driver). For example, the braking driver 36 is constituted by a motor and a gear, etc., and the second braking component 33 is linked to the braking driver 36 via a linking component 38. In FIG. 9A, the linking component 38 is rotated around its upper shaft 38a by the braking driver 36, and the second braking component 33 is fixed to the lower part of the linking component 38.

Figure 9B:
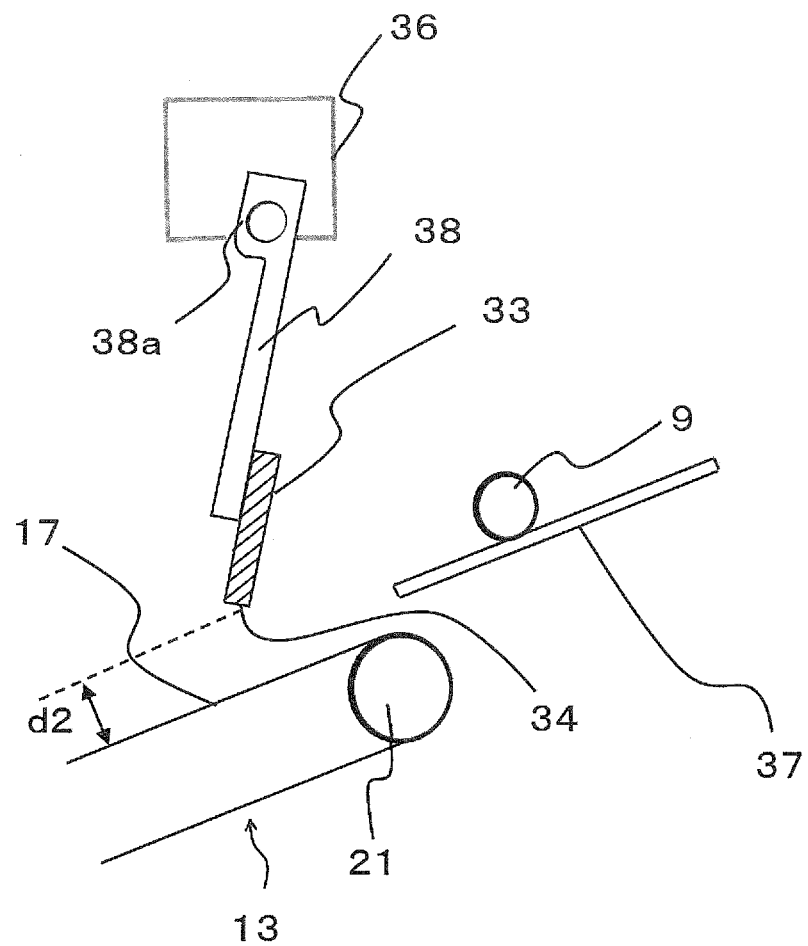
FIG. 9B is a schematic diagram of the area near a second braking component of the removal head in Embodiment 1 of the present invention.

FIG. 9B shows a state in which the second braking component 33 has moved from near the area above the guide path 37. As shown in FIG. 9B, if the second braking component 33 rotates to the movement path component 13 side (see the arrow B), the distance d2 by which the end 34 of the second braking component 33 moves away from the movement path component 13 should be greater than the diameter of the pharmaceutical container 9. Doing this allows the pharmaceutical container 9, whose movement has been stopped by the second braking component 33, to be moved downward again.

Thus providing the second braking component 33 allows the pharmaceutical container 9 that has rolled out of the pharmaceutical container holding cassette 4 to be temporarily stopped by the second braking component 33. That is, since the second braking component 33 can temporarily stop the movement of the pharmaceutical container 9, the movement speed of the pharmaceutical container 9 can subsequently be reduced as it reaches the contact component 20 of the first braking component 14.

Therefore, this prevents a situation in which the movement speed of the pharmaceutical container 9 is too high as it reaches the contact component 20 of the first braking component 14, causing it to go up and over the first braking component 14, or the pharmaceutical container 9 is damaged by the impact resulting when the pharmaceutical container 9 is stopped by the first braking component 14.

Control System of Pharmaceutical Dispensing Apparatus

Figure 10:
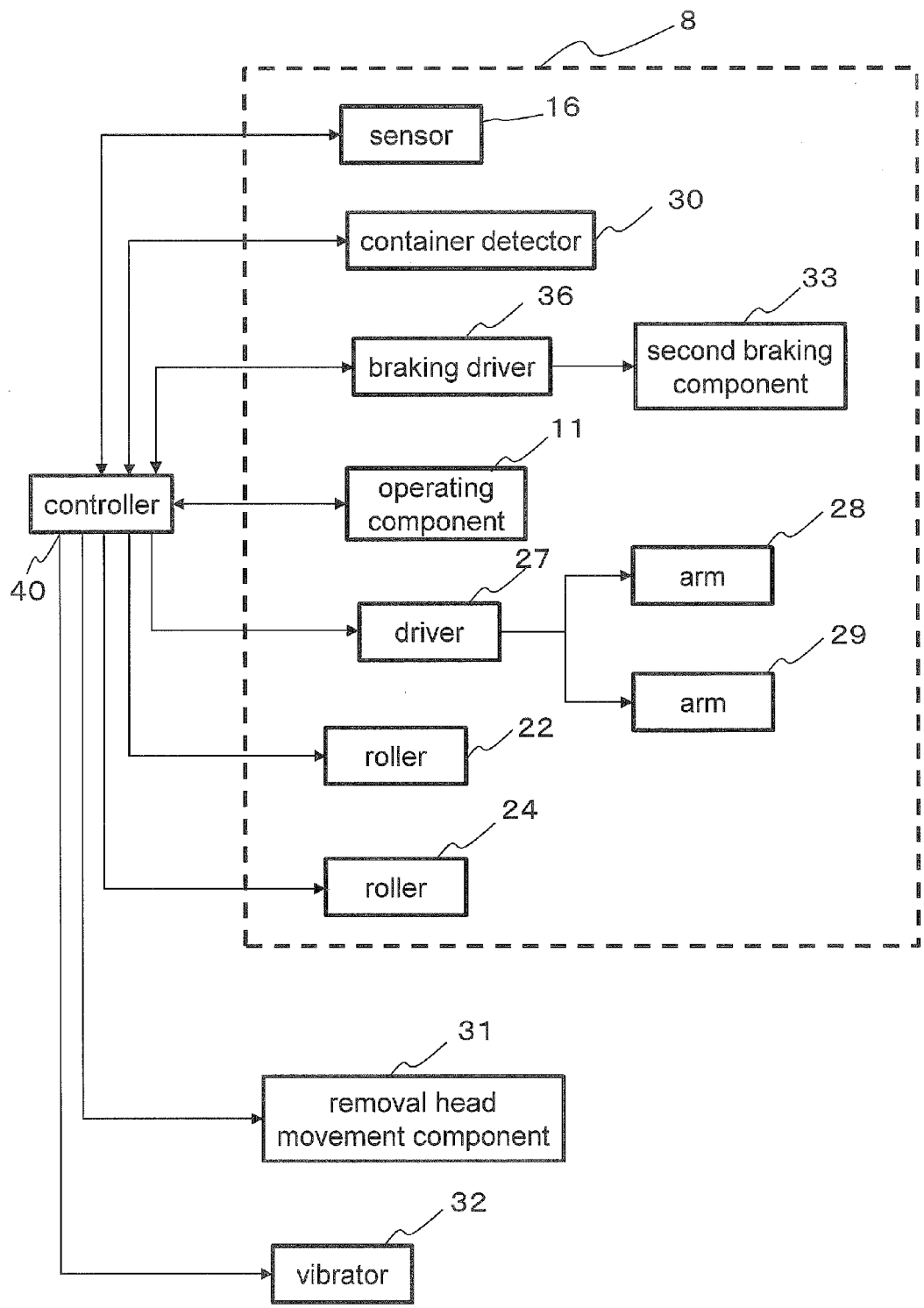
FIG. 10 is a block diagram of the control configuration of the pharmaceutical dispensing apparatus in Embodiment 1 of the present invention.

FIG. 10 is a control block diagram of the pharmaceutical dispensing apparatus in this embodiment.

The pharmaceutical dispensing apparatus in this embodiment comprises a controller 40. As shown in FIG. 9, the controller 40 controls the operation of the sensor 16, the container detector 30, the roller 22, the roller 24, the driver 27, the braking driver 36, the removal head movement component 31, the operating component 11, the vibrator 32, and so on. The braking driver 36 drives the second braking component 33.

To describe this in further detail, the controller 40 stops the operation of the roller 22 and the roller 24 upon receiving the reading result of the identification label 15 by the sensor 16. Furthermore, the controller 40 receives the detection result from the container detector 30, and operates the vibrator 32 when the presence of the pharmaceutical container 9 is detected.

2. Operation

With the pharmaceutical dispensing apparatus in this embodiment, configured as above, when a pharmaceutical container is dispensed using the removal head 8 shown in FIG. 4 (an example of a pharmaceutical dispensing unit), the following operation is executed.

Overview of Operation of Pharmaceutical Dispensing Apparatus

First, as shown in FIG. 4, an operation is executed to take the pharmaceutical container 9 out of the pharmaceutical container holding cassette 4, but since this operation is a well known operation, it will only be described briefly, to avoid making the description overly complicated.

That is, when the removal lever 10 of the pharmaceutical container holding cassette 4 is operated by the operating component 11, the pharmaceutical container 9 held in the pharmaceutical container holding cassette 4 is taken out of the pharmaceutical container holding cassette 4 as shown in FIG. 4, and rolls toward the movement path component 13 shown in FIG. 5 via the removal lever 10 and the guide path 37.

When the pharmaceutical container 9 reaches the movement path component 13 and comes into contact with the movement face 17 of the movement path component 13, the pharmaceutical container 9 is following over the movement face 17 of the movement path component 13 while being decelerated, while its rotation in the counter-clockwise direction in FIG. 4 (see the arrow C in FIG. 5) is assisted.

That is, in this embodiment, the movement face 17 of the movement path component 13 moves upward and to the right in FIG. 4, and moves in the opposite direction from the movement direction of the pharmaceutical container 9 as it rolls out of the pharmaceutical container holding cassette 4. Therefore, contact between the movement face 17 and the pharmaceutical container 9 exerts a force on the pharmaceutical container 9 in the direction that hinders its rolling, and this reduces its movement speed.

The pharmaceutical container 9 is moving downward and to the left in FIG. 4 over the movement face 17 of the movement path component 13 while being decelerated until it reaches the first braking component 14 provided to the end of the movement path component 13. That is, the pharmaceutical container 9 is moved by the action of gravity.

Once the pharmaceutical container 9 reaches the first braking component 14, the movement of the pharmaceutical container 9 is stopped. That is, as shown in FIG. 4, the movement face 19 of the first braking component 14 is formed as an inclined face that slopes downward and to the right so as to impede the movement of the pharmaceutical container 9, and the movement of the pharmaceutical container 9 is stopped by this movement face 19.

In this case, if the angle of the movement face 19 of the first braking component 14 is increased so that it is close to vertical, the moving pharmaceutical container 9 will be more reliably stopped at the movement face 19, but on the other hand, the pharmaceutical container 9 will be subjected to a greater impact when its movement is stopped, and this can lead to damage of the pharmaceutical container 9.

In contrast, if the angle of the movement face 19 of the first braking component 14 is decreased so that it is close to horizontal, the pharmaceutical container 9 will be subjected to less impact when its movement is stopped, but on the other hand, the moving pharmaceutical container 9 will be less reliably stopped at the movement face 19. That is, the energy at which the pharmaceutical container 9 moves will be greater, and this can cause the pharmaceutical container 9 to go up and over the first braking component 14.

In order to solve the above-mentioned mutually conflicting problems, in this embodiment the movement face 19 of the first braking component 14 is further moved downward and to the right in FIG. 4, and is moved in the opposite direction from the movement direction of the pharmaceutical container 9 that rolls out of the pharmaceutical container holding cassette 4. Therefore, when the movement face 19 and the pharmaceutical container 9 come into contact, a force is exerted on the pharmaceutical container 9 in the direction that hinders movement, so this movement can be effectively stopped.

The result of this is that the angle of the movement face 19 of the first braking component 14 can be reduced to decrease the impact to which the pharmaceutical container 9 is subjected when its movement stops, and the moving pharmaceutical container 9 can be more reliably stopped at the movement face 19.

In a state in which the movement of the pharmaceutical container 9 has been stopped by the first braking component 14, the contact component 18 of the movement face 17 comes into contact with the outer peripheral part of the pharmaceutical container 9 and rotates the pharmaceutical container 9. In this embodiment, the movement face 17 moves upward and to the right in FIG. 4, and the pharmaceutical container 9 is rotated counter-clockwise by the contact component 18.

The identification label 15 affixed to the pharmaceutical container 9 is pointed toward the sensor 16 shown in FIG. 4 as the pharmaceutical container 9 rotates. That is, in this embodiment it is pointed upward in FIG. 4.

The sensor 16 reads pharmaceutical information about the pharmaceutical held in the pharmaceutical container 9 from the identification label 15 affixed to the pharmaceutical container 9.

Once the pharmaceutical information on the pharmaceutical container 9 has been read by the sensor 16 and it has been confirmed that it matches the pharmaceutical indicated by the prescription, the pharmaceutical container 9 is put into the holding pocket 12.

Specifically, in this embodiment the driver 27 is provided to produce a specific gap between the first braking component 14 and the end 13a of the movement path component 13. That is, this driver 27 produces a specific gap between the first braking component 14 and the end 13a of the movement path component 13 by moving the movement path component 13 to the right in FIG. 4 (see the arrow A direction), for example.

The gap produced by the driver 27 should be enough to provide a space that is larger than the width of the pharmaceutical container 9 in the direction that is perpendicular to the lengthwise direction of the pharmaceutical container 9.

The pharmaceutical container 9 is then allowed to freely roll down through the space produced by the driver 27, and drops into the holding pocket 12 provided under the first braking component 14. The pharmaceutical container 9 is temporarily held stored in this holding pocket 12.

After the set of pharmaceutical containers 9 indicated by the prescription have been put into the holding pocket 12 by this same operation, the pharmaceutical containers 9 are put on the trays 5 by lowering the removal head 8 as discussed above through reference to FIG. 3.

Detailed Operation of Pharmaceutical Dispensing Apparatus

Figure 11:
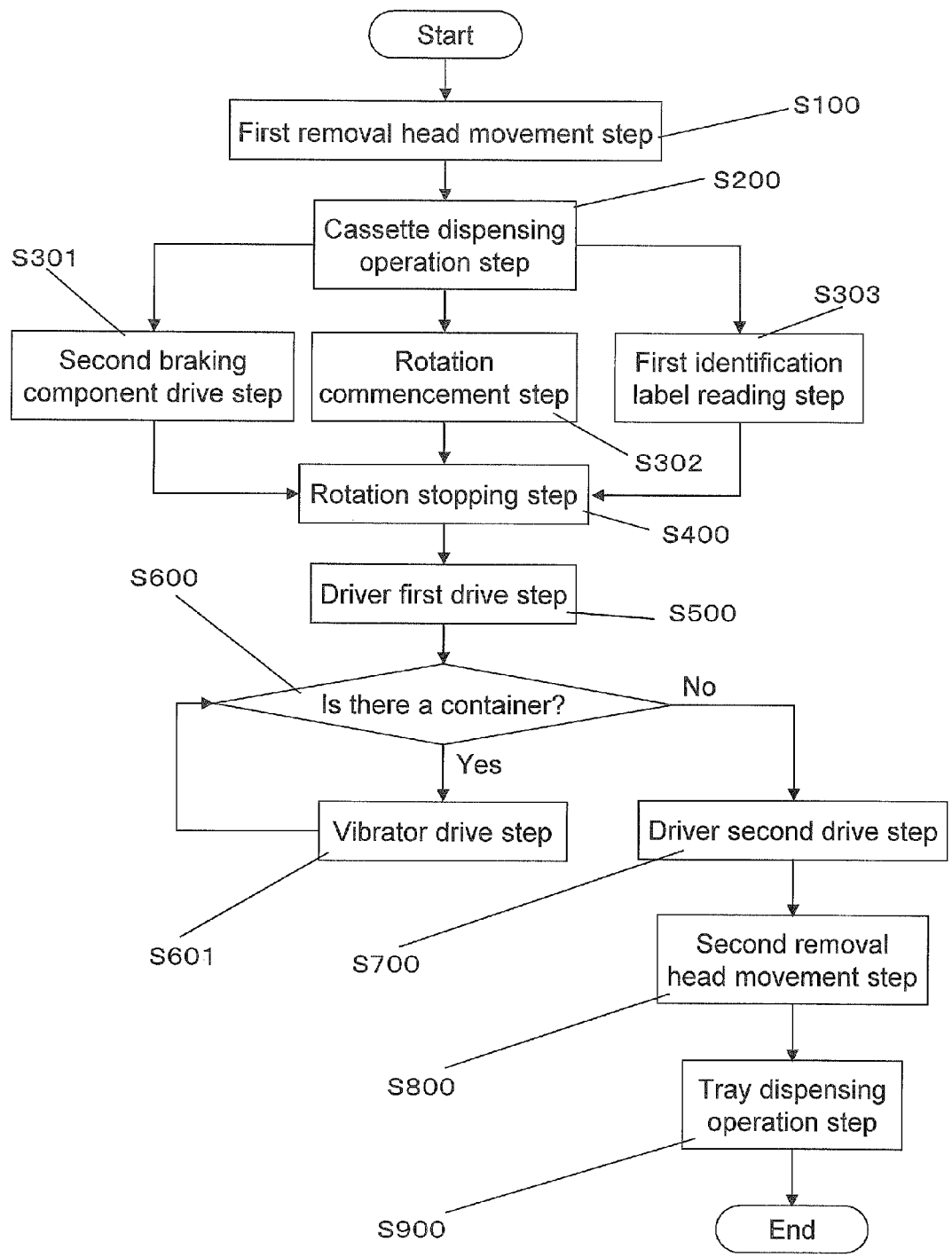
FIG. 11 is an overall operational flowchart of the pharmaceutical dispensing apparatus in Embodiment 1 of the present invention.

The operation of the removal head 8 in this embodiment, and a pharmaceutical dispensing apparatus comprising the removal head 8, will now be described in detail. FIG. 11 shows the operational flow of the pharmaceutical dispensing apparatus in this embodiment. As shown in FIG. 11, the operation of the removal head 8 in this embodiment can be broadly broken down into the following steps 1 to 12.

(1) First removal head movement step S100
(2) Cassette dispensing operation step S200
(3) Second braking component drive step S301
(4) Rotation commencement step S302
(5) First identification label reading step S303
(6) Rotation stopping step S400
(7) Driver first drive step S500
(8) Container detection step S600
(9) Vibrator drive step S601
(10) Driver second drive step S700
(11) Second removal head movement step S800
(12) Tray dispensing operation step S900

The above-mentioned steps 1 to 12 will now be described in detail.

(1) First Removal Head Movement Step S100

First, the controller 40 drives the removal head movement component 31 shown in FIG. 3, and moves the removal head 8 to the rear face at the location of the pharmaceutical container holding cassette 4 that stores the pharmaceutical container 9 indicated from outside the pharmaceutical dispensing apparatus, or more specifically, the one indicated by a prescription, etc.

(2) Cassette Dispensing Operation Step S200

After the first removal head movement step S100 discussed above, the controller 40 operates the removal lever 10 of the pharmaceutical container holding cassette 4 with the operating component 11 of the removal head 8 as shown in FIG. 4. This operation causes the pharmaceutical container 9 held in the pharmaceutical container holding cassette 4 to be taken out to the removal head 8 side from the pharmaceutical container holding cassette 4.

(3) Second Braking Component Drive Step S301

Next, the second braking component drive step S301 will be described.

After the cassette dispensing operation step S200, the controller 40 performs the second braking component drive step S301 simultaneously with the below mentioned rotation commencement step S302 and the rotation commencement step S302.

After the pharmaceutical container 9 has been taken out of the pharmaceutical container holding cassette 4, the pharmaceutical container 9 is temporarily stopped (see FIG. 9A) by the end 34 of the second braking component 33 (an example of a second braking component) provided to the removal head 8. Specifically, the braking driver 36 is controlled by the controller 40 so that the end 34 of the second braking component 33 is located near the upper face of the guide path 37. After this, the controller 40 drives the second braking component 33 to form a space at the end 34 of the second braking component 33, and moves (rolls) the temporarily stopped pharmaceutical container 9 to the movement path component 13 side.

(4) Rotation Commencement Step S302

After the cassette dispensing operation step S200, the controller 40 performs the rotation commencement step S302 simultaneously with the above mentioned second braking component drive step S301 and the below mentioned first identification label reading step S303.

In this second braking component drive step S301, the controller 40 drives the roller 22 shown in FIG. 4, and continuously moves the movement face 17 of the movement path component 13 upward and to the right in FIG. 4 (see the arrow D in FIG. 7). This reduces the movement speed (rolling speed) of the pharmaceutical container 9 when it moves (rolls) from the end 34 of the second braking component 33. Along with this, the pharmaceutical container 9 is rotated at the contact component 20 of the first braking component 14 within the removal head 8.

Furthermore, at the same time, in the steps of this embodiment, the controller 40 drives the roller 24 and continuously moves the movement face 19 of the first braking component 14 (an example of a first braking component) downward and to the right in FIG. 4 (see the arrow E in FIG. 7). Specifically, it is continuously moved in the opposite direction from the movement direction of the pharmaceutical container 9 as it rolls down from the second braking component 33 side.

This stops the pharmaceutical container 9 at the contact component 20 of the first braking component 14 within the removal head 8, and also allows the pharmaceutical container 9 to be rotated more stably.

In the initial state of this step, the space between the movement path component 13 and the first braking component 14 is closed, so in this step the pharmaceutical container 9 does not drop down (move) toward the holding pocket 12.

That is, as shown in FIGS. 4 and 5, in this embodiment, in a state in which the pharmaceutical container 9 is stopped at a position where it is in contact with the contact component 20 of the first braking component 14 within the removal head 8, the roller 22 is rotated, which moves the movement face 17 upward and to the right in FIG. 4, that is, in the reverse direction from the direction in which the pharmaceutical container 9 moves over the movement face 17 from the pharmaceutical container holding cassette 4 side to the holding pocket 12 side. This allows the pharmaceutical container 9 to be rotated on the contact component 20 of the first braking component 14 within the removal head 8. In this embodiment, rotation is the counter-clockwise direction, as shown in FIG. 5.

(5) First Identification Label Reading Step S303

After the above-mentioned cassette dispensing operation step S200, the controller 40 performs the first identification label reading step S303 simultaneously with the above-mentioned second braking component drive step S301 and the rotation commencement step S302.

In this second braking component drive step S301, the controller 40 controls the sensor 16 and reads the identification label 15 on the rotating pharmaceutical container 9.

(6) Rotation Stopping Step S400

When the controller 40 performs the above-mentioned first identification label reading step S303, and reads the identification label 15 on the rotating pharmaceutical container 9, the controller 40 stops the rotation of the roller 22 and the roller 24, which were rotated in the above-mentioned rotation commencement step S302.

This stops the rotation of the pharmaceutical container 9 that was rotating on the contact component 20 of the first braking component 14.

(7) Driver First Drive Step S500

When the controller 40 performs the above-mentioned rotation stopping step S400 and confirms that the rotation of the roller 22 and the roller 24 has stopped, it drives the driver 27 to produce a specific space between the first braking component 14 and the end 13a of the movement path component 13. That is, a space is opened up between the movement path component 13 and then first braking component 14. This causes the pharmaceutical container 9 stopped at a position in contact with the contact component 20 of the first braking component 14 to drop down toward the holding pocket 12 provided under the first braking component 14, and the pharmaceutical container 9 is held in the holding pocket 12.

(8) Container Detection Step S600

After the controller 40 performs the above-mentioned first drive step S500 for the driver 27, and opens up a space between the movement path component 13 and the first braking component 14, it controls the container detector 30 to detect whether or not the pharmaceutical container 9 is in the container detection region K (whether it is present or absent).

The container detector 30 here is disposed so that the container detection region K of the container detector 30 is on the contact component 20 of the first braking component 14, as discussed above (see FIG. 8).

Doing this confirms whether or not the pharmaceutical container 9 is held in the holding pocket 12.

Figure 12:
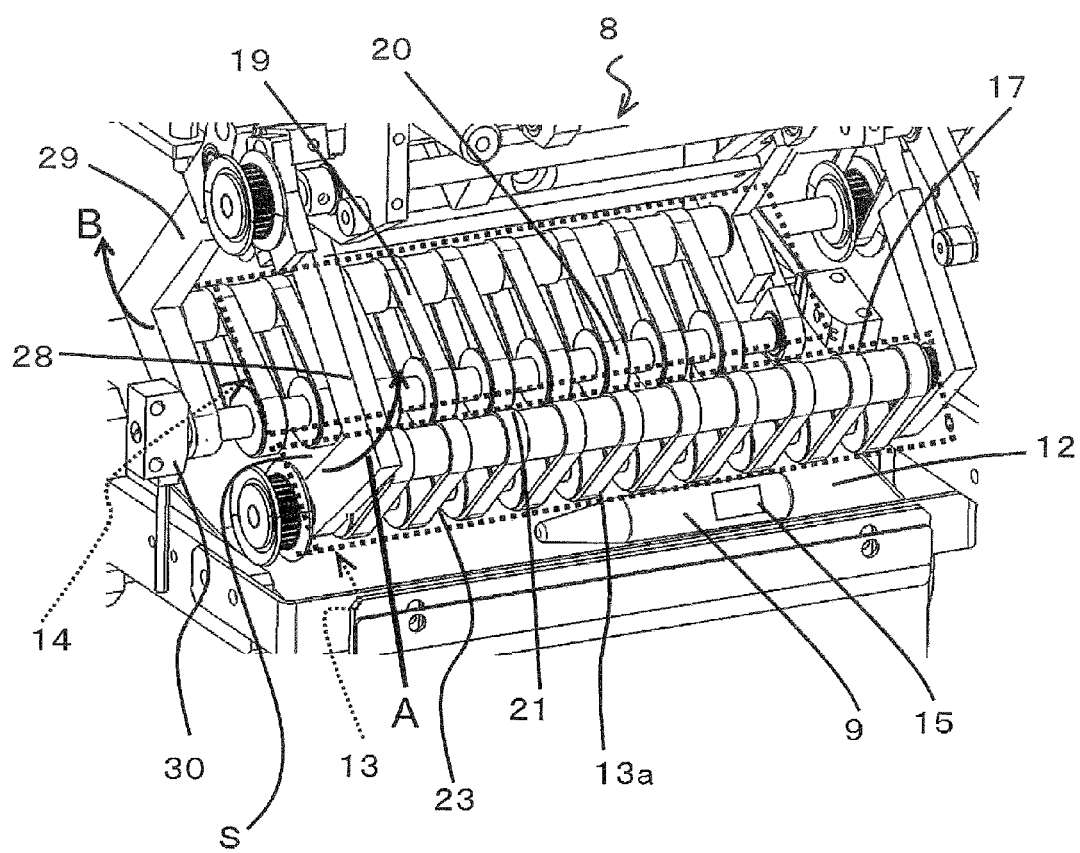
FIG. 12 is an oblique view illustrating the operation of the main parts of the removal head pertaining to Embodiment in the present invention.

That is, as shown in FIG. 12, in the driver first drive step S500 and the container detection step S600, a space is opened up between the movement path component 13 and the first braking component 14, that is, there is a space S between the movement path component 13 and the first braking component 14, so the pharmaceutical container 9 drops through this space into the holding pocket 12. Therefore, in the ordinary state shown in FIG. 12, the container detector 30 detects that the pharmaceutical container 9 is not on the contact component 20 of the first braking component 14, or in other words, that there is no pharmaceutical container 9 in the space S portion between the movement path component 13 and the first braking component 14. After this, the controller 40 drives the driver 27 to close up the space between the movement path component 13 and the first braking component 14.

After the container detector 30 has detected that there is no pharmaceutical container 9, the driver 27 is driven so as to close up the space between the movement path component 13 and the first braking component 14, and this reliably confirms whether or not the pharmaceutical container 9 has moved (been dispensed) into the holding pocket 12. Also, since the space between the movement path component 13 and the first braking component 14 is closed once the absence of a pharmaceutical container 9 has been confirmed, damage to the pharmaceutical container 9 can be prevented. As a result, the pharmaceutical container 9 can be moved (dispensed) more reliably into the holding pocket 12.

There may be variance in how long it takes the pharmaceutical container 9 to drop into the holding pocket 12 due to differences in the shape, size, and weight of the pharmaceutical containers 9, but if no container detector 30 were provided, the pharmaceutical container 9 that takes the longest time to drop would have to be used as a reference. Specifically, even if a pharmaceutical container 9 with a short drop time is used, the space between the movement path component 13 and the first braking component 14 will have to be closed after waiting for the longest drop time to elapse. However, if the system is controlled so that the driver 27 is driven and the space between the movement path component 13 and the first braking component 14 is closed after the container detector 30 has detected that there is no pharmaceutical container 9, then the space between the movement path component 13 and the first braking component 14 can be closed up as soon as possible, so the time it takes to dispense the pharmaceutical containers 9 can be shortened.

(9) Vibrator Drive Step S601

The controller 40 performs the container detection step S600, and detects whether or not a pharmaceutical container 9 is in the container detection region K (whether it is present or absent). However, as mentioned above, usually the pharmaceutical container 9 goes through the space between the movement path component 13 and the first braking component 14 and is held in the holding pocket 12 in a state in which it is lying on its side (see FIG. 12). Therefore, in the ordinary operating state in which the pharmaceutical container 9 drops into the holding pocket 12, the pharmaceutical container 9 will never be detected to be within the container detection region K in the above-mentioned container detection step S600.

Figure 13:
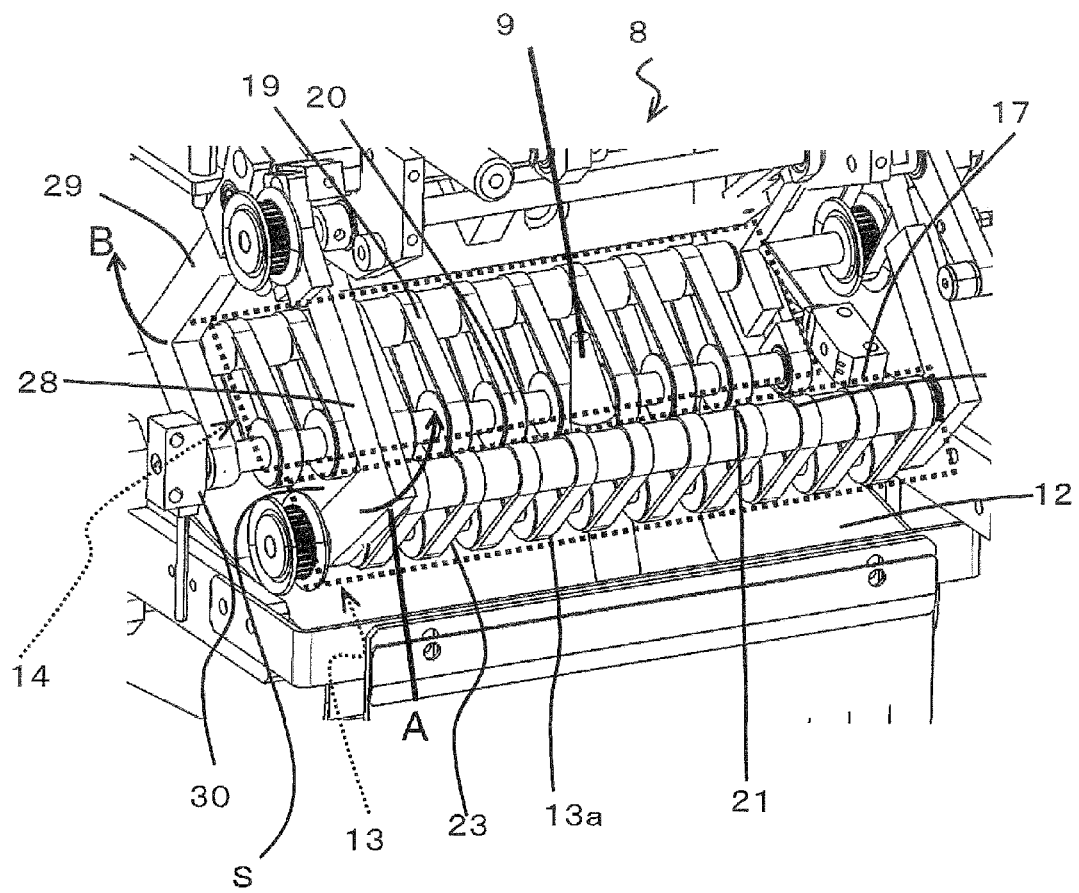
FIG. 13 is an oblique view illustrating the operation of the main parts of the removal head pertaining to Embodiment in the present invention.

However, as shown in FIG. 13, the pharmaceutical container 9 may not completely pass through the space between the movement path component 13 and the first braking component 14, such as when the pharmaceutical container 9 is standing up in the holding pocket 12. In such a case, the controller 40 uses the container detector 30 to detect that the pharmaceutical container 9 is within the container detection region K.

Thus, in the above-mentioned container detection step S600, if the pharmaceutical container 9 is detected within the container detection region K, the controller 40 drives the vibrator 32 (shown in FIG. 3) and vibrates the entire removal head 8 (S601).

Thus vibrating the vibrator 32 and vibrating the entire removal head 8 knocks over the pharmaceutical container 9 that was standing upright in the holding pocket 12, and allows it to lie on its side in the holding pocket 12. Specifically, a state can be achieved in which the pharmaceutical container 9 more reliably passes through the space S between the movement path component 13 and the first braking component 14. That is, a state can be achieved in which the pharmaceutical container 9 is not in the container detection region K, as shown in FIG. 12.

After the vibrator drive step S601 has thus been performed, the controller 40 performs the above-mentioned container detection step S600, and confirms that the pharmaceutical container 9 is not in the container detection region K.

(10) Driver Second Drive Step S700

After the controller 40 performs the above-mentioned container detection step S600 and detects that the pharmaceutical container 9 is not in the container detection region K, it drives the driver 27 shown in FIG. 5 and closes up the space between the movement path component 13 and the first braking component 14.

(11) Second Removal Head Movement Step S800

After the controller 40 has performed the above-mentioned container detection step S600 and closed up the space between the movement path component 13 and the first braking component 14, it drives the removal head movement component 31 and moves the removal head 8 over the tray 5 as shown in FIG. 3.

(12) Tray Dispensing Operation Step S900

After the controller 40 has performed the above-mentioned second removal head movement step S800 and moved the removal head 8 over the tray 5, it drives the holding pocket 12 to move (dispense) the pharmaceutical container 9 inside the holding pocket 12 into the tray 5.

As discussed above, in this embodiment, the movement of the pharmaceutical container 9 that has moved along the movement path component 13 is stopped at a specific location by the first braking component 14, and the pharmaceutical container 9 is rotated by the contact component 18 having the movement face 17. That is, since the movement face 17 moves along the movement path of the pharmaceutical container 9, the pharmaceutical container 9 can be smoothly rotated by the contact component 18.

Therefore, the identification label 15 can be pointed toward the sensor 16 by rotating the pharmaceutical container 9, and the identification label 15 on the pharmaceutical container 9 can be read more reliably by the sensor 16, the result of which is better reliability.

Also, because the removal head 8 (an example of a pharmaceutical dispensing unit) is provided with the movement path component 13 that moves the pharmaceutical container 9 removed from the pharmaceutical container holding cassette 4, the first braking component 14 that is provided to the end 13a of the movement path component 13 that stops the pharmaceutical container 9 that has moved along the movement path component 13 at a specific location, the driver 27 that drops the pharmaceutical container 9 by driving at least one of the movement path component 13 and the first braking component 14 and opening and closing the space between the movement path component 13 and the first braking component 14, the container detector 30 that detects the presence or absence of the pharmaceutical container 9 at the above-mentioned specific location, and a controller that controls the driver 27 according to the result of the container detector 30, it can be confirmed whether or not the movement (dispensing) of pharmaceutical containers in a pharmaceutical dispensing apparatus has been performed properly.

3. Main Features (3-1)

The removal head 8 (an example of a pharmaceutical dispensing unit) in this embodiment comprises the movement path component 13, the first braking component 14 (an example of a first braking component), and the sensor 16. The movement path component 13 moves the pharmaceutical container 9 removed from the pharmaceutical container holding cassette 4 (an example of a cassette) that holds a substantially cylindrical pharmaceutical container 9 having an identification label 15 (an example of a first identification label) indicating pharmaceutical information. The first braking component 14 is provided to the end 13a of the movement path component 13, and stops the pharmaceutical container 9 that has moved along the movement path component 13 at a specific location. The sensor 16 reads the identification label 15 on the pharmaceutical container 9 whose movement has been stopped at a specific location by the first braking component 14. The movement path component 13 has the movement face 17 (an example of a first movement face) that moves along the movement path of the pharmaceutical container 9, and the movement face 17 has the contact component 18 (an example of a first contact component) that comes into contact with the pharmaceutical container 9.

The "specific location" can be considered a location on the end 13a of the movement path component 13, where there is contact with the first braking component 14.

Consequently, the movement of the pharmaceutical container 9 that has moved along the movement path component is stopped at a specific location by the first braking component 14, and the pharmaceutical container 9 is rotated by the contact component 18 which the movement face 17 has. That is, since the movement face 17 moves along the movement path of the pharmaceutical container 9, the pharmaceutical container 9 can be smoothly rotated by the contact component 18.

Therefore, the identification label 15 can be pointed toward the sensor 16, the performance of the sensor 16 in reading the identification label 15 on the pharmaceutical container 9 is enhanced, and as a result reliability can be improved.

(3-2)

The movement face 17 in the removal head 8 (an example of a pharmaceutical dispensing unit) in this embodiment moves in the opposite direction from the movement direction of the pharmaceutical container 9.

Consequently, when the pharmaceutical container 9 removed from the pharmaceutical container holding cassette 4 moves while rolling over the movement face 17 of the movement path component 13, a force is exerted on the pharmaceutical container 9 in the opposite direction from the movement direction of the pharmaceutical container 9.

Accordingly, the movement speed of the pharmaceutical container 9 can be reduced, and it can be stopped more reliably at a specific location.

(3-3)

The first braking component 14 in the removal head 8 (an example of a pharmaceutical dispensing unit) in this embodiment has the movement face 19 (an example of a second movement face) that moves in the opposite direction from the movement direction of the pharmaceutical container 9, and the movement face 19 has the contact component 20 (an example of a second contact component) that comes into contact with the pharmaceutical container 9.

Consequently, when the pharmaceutical container 9 moves while rolling over the movement face 17 of the movement path component 13, the first braking component 14 exerts a force on the pharmaceutical container 9 in the opposite direction from the movement direction of the pharmaceutical container 9.

The movement of the pharmaceutical container 9 can be reduced and the pharmaceutical container 9 can be stopped more reliably at a specific location, and the rotation direction of the pharmaceutical container 9 in the state shown in FIG. 5 is counter-clockwise as seen in the arrow G direction, the pharmaceutical container 9 can be rotated, and the performance of the sensor 16 in reading the identification label 15 on the pharmaceutical container 9 can be improved.

(3-4)

The movement path component 13 of the removal head 8 in the above embodiment has the roller 21 (an example of a first roller), the roller 22 (an example of a second roller), and the first belts 23 (an example of first belts). The roller 21 is provided on the pharmaceutical container holding cassette 4 side, between the first braking component 14 and the pharmaceutical container holding cassette 4. The roller 22 is provided lower than the roller 21 and more to the first braking component 14 side than the roller 21. The first belts 23 go between the roller 21 and the roller 22. At least one of the roller 21 and the roller 22 is driven to rotate the first belts 23 between the roller 21 and the first belts 23, and this forms the movement face 17.

Because the movement face 17 can be formed in this way, the pharmaceutical container 9 can be moved while decelerating.

(3-5)

Also, the first braking component 14 of the removal head 8 in the above embodiment has the roller 24 (an example of a third roller), the roller 25 (an example of a fourth roller), and the second belts 26. The roller 24 is provided to the rear of the movement face 17 in the movement direction of the pharmaceutical container 9. The roller 25 is provided at a location that is above the roller 24 and further to the rear of the roller 24. The second belts 26 go between the roller 24 and the roller 25. At least one of the roller 24 and the roller 25 is driven to rotate the second belts 26 between the roller 24 and the roller 25, and this forms the movement face 19.

Because the movement face 19 can be formed in this way, the pharmaceutical container 9 can be stopped more reliably at a specific location.

(3-6)

Also, with the removal head 8 in the above embodiment, a plurality of the first belts 23 are provided, and these first belts 23 go between the roller 21 and the roller 22, separated from each other at a specific spacing. A plurality of the second belts 26 are provided, and these second belts 26 go between the roller 24 and the roller 25, separated from each other at a specific spacing. Consequently, the movement face 17 and the movement face 19 are formed so as to be divided.

(3-7)

Also, as shown in FIG. 7, with the removal head 8 in the above embodiment, the ends 23A of the first belts 23 are disposed in the spaces in between the second belts 26, and the ends 26A of the second belts 26 are disposed in the spaces in between the first belts 23. The ends 23A of the first belts 23 and the ends 26A of the second belts 26 intersect when viewed in a direction parallel to both the movement face 17 and the movement face 19.

Thus disposing the ends 23A of the first belts 23 and the ends 26A of the second belts 26 alternating in a direction perpendicular to the movement direction of the pharmaceutical container 9 allows the force exerted on the pharmaceutical container 9 by the first belts 23 and the force exerted on the pharmaceutical container 9 by the second belts 26 to be substantially equal along the lengthwise direction of the pharmaceutical container 9, and allows the pharmaceutical container 9 to be rotated stably around a direction perpendicular to the movement direction.

(3-8)

Also, the removal head 8 in the above embodiment further comprises the second braking component 33 (an example of a second braking component) that temporarily stops the movement of the pharmaceutical container 9 at a specific location between the first braking component 14 and the pharmaceutical container holding cassette 4.

Thus temporarily stopping the pharmaceutical container 9 between the first braking component 14 and the pharmaceutical container holding cassette 4 allows the movement speed of the pharmaceutical container 9 to be reduced, so the pharmaceutical container 9 can be stopped more reliably.

(3-9)

Also, the removal head 8 in the above embodiment comprises the driver 27 and the holding pocket 12 (an example of a holding component). The driver 27 produces a specific space between the first braking component 14 and the end 13a of the movement path component 13. The holding pocket 12 holds the pharmaceutical container 9 that has dropped in from the specific space produced by the driver 27.

Thus creating a specific space between the first braking component 14 and the end 13a of the movement path component 13 allows the pharmaceutical container 9 to be put directly in the holding pocket 12 from the specific location where the pharmaceutical container 9 has stopped for the purpose of sensing the identification label 15.

(3-10)

Also, the pharmaceutical dispensing apparatus in the above embodiment comprises the removal head 8 and the controller 40. The removal head 8 has the driver 27 and the container detector 30. The driver 27 drives at least one of the movement path component 13 and the first braking component 14 to open and close the space between the movement path component 13 and the first braking component 14, which allows the pharmaceutical container 9 to drop. The container detector 30 detects the presence or absence of the pharmaceutical container 9 at the specific location. The controller 40 controls the driver 27 according to the detection result from the container detector.

Consequently, if the pharmaceutical container 9 does not drop from the specific location into the holding pocket 12, for example, the closing up of the space between the movement path component 13 and the first braking component 14 can be prevented, and this helps avoid damage to the pharmaceutical container 9 and so forth.

(3-11)

The pharmaceutical dispensing apparatus in this embodiment further comprises the vibrator 32 that vibrates at least one of the movement path component 13 and the first braking component 14. The controller 40 puts the space between the movement path component 13 and the first braking component 14 into an open state, and drives the vibrator 32 when the container detector 30 has detected a pharmaceutical container 9.

Consequently, even if the pharmaceutical container 9 has not dropped down through the space between the movement path component 13 and the first braking component 14, vibration can be applied to drop that pharmaceutical container 9 into the holding pocket 12. Accordingly, there is no need for the user to take out the pharmaceutical container 9, etc., which makes the apparatus more convenient to use.

(3-12)

The method for controlling the pharmaceutical dispensing apparatus in this embodiment is a method for controlling a pharmaceutical dispensing apparatus having the movement path component 13 and the first braking component 14, and comprises the cassette dispensing operation step S200 (an example of a removal step), the rotation commencement step S302 (an example of a movement step), and the first identification label reading step S303 (an example of a reading step). The movement path component 13 moves a substantially cylindrical pharmaceutical container 9 that has an identification label 15 and has been removed from the pharmaceutical container holding cassette 4 that holds the pharmaceutical containers 9. The first braking component 14 is provided to the end 13a of the movement path component 13, and stops a pharmaceutical container that has moved along the movement path component 13 at a specific location. The movement path component 13 has the movement face 17 that moves along the movement path of the pharmaceutical container 9, and the movement face 17 has the contact component 18 that comes into contact with the pharmaceutical container 9. The cassette dispensing operation step S200 involves taking the pharmaceutical container 9 out to the removal head 8 side. The rotation commencement step S302, the movement face 17 involves moving. The first identification label reading step S303 involves reading the identification label 15 on the pharmaceutical container 9 whose movement after removal has been stopped at a specific location by the first braking component 14.

In the first identification label reading step S303, the identification label 15 is read while the pharmaceutical container 9 is rotated at the specific location by the movement of the movement face 17.

Consequently, movement of a pharmaceutical container 9 that has moved along the movement path component 13 is stopped at a specific location by the first braking component 14, and the pharmaceutical container 9 is rotated by the contact component 18 had by the movement face 17. That is, since the movement face 17 moves along the movement path of the pharmaceutical container 9, the pharmaceutical container 9 can be smoothly rotated by the contact component 18.

Therefore, the identification label 15 can be pointed in the direction of the sensor 16, the performance of the sensor 16 in reading the identification label 15 on the pharmaceutical container 9 can be improved, and this results in better reliability.

(3-13)

The method for controlling the pharmaceutical dispensing apparatus in this embodiment comprises the first drive step S500 (an example of a first drive step), the container detection step S600 (an example of a container detection step), and the second drive step S700 (an example of a second drive step). The first drive step S500 involves moving at least one of the movement path component 13 and the first braking component 14, and opening up the space between the movement path component 13 and the first braking component 14.

The container detection step S600 involves detecting the presence or absence of a pharmaceutical container 9 at a specific location after the first drive step S500. The second drive step S700 involves closing the space between the movement path component 13 and the first braking component 14 if no pharmaceutical container 9 was detected in the container detection step S600.

Consequently, this prevents the space between the movement path component 13 and the first braking component 14 from being closed if pharmaceutical container 9 has not dropped into the holding pocket 12 from the specific location, etc., and this helps avoid damage to the pharmaceutical container 9 and so forth.

(3-14)

The method for controlling the pharmaceutical dispensing apparatus in this embodiment comprises the vibrator drive step S601 (an example of a vibration step). The vibrator drive step S601 involves vibrating at least one of the movement path component 13 and the first braking component 14 if a pharmaceutical container 9 was detected in the container detection step S600.

Consequently, even if pharmaceutical container 9 has not dropped down through the space between the movement path component 13 and the first braking component 14, vibration can be applied to drop that pharmaceutical container 9 into the holding pocket 12. Accordingly, there is no need for the user to take out the pharmaceutical container 9, etc., which makes the apparatus more convenient to use.

4. Other Embodiments (A)

Other embodiments related to the movement faces 17 and 19 will now be discussed.

(A-1)

With the removal head 8 in the above embodiment, the angles of the movement face 17 and the movement face 19 are fixed, but the configuration may be such that at least one of the angle of the movement face 17 and the angle of the movement face 19 can be varied according to the type of pharmaceutical container 9.

Figure 14:
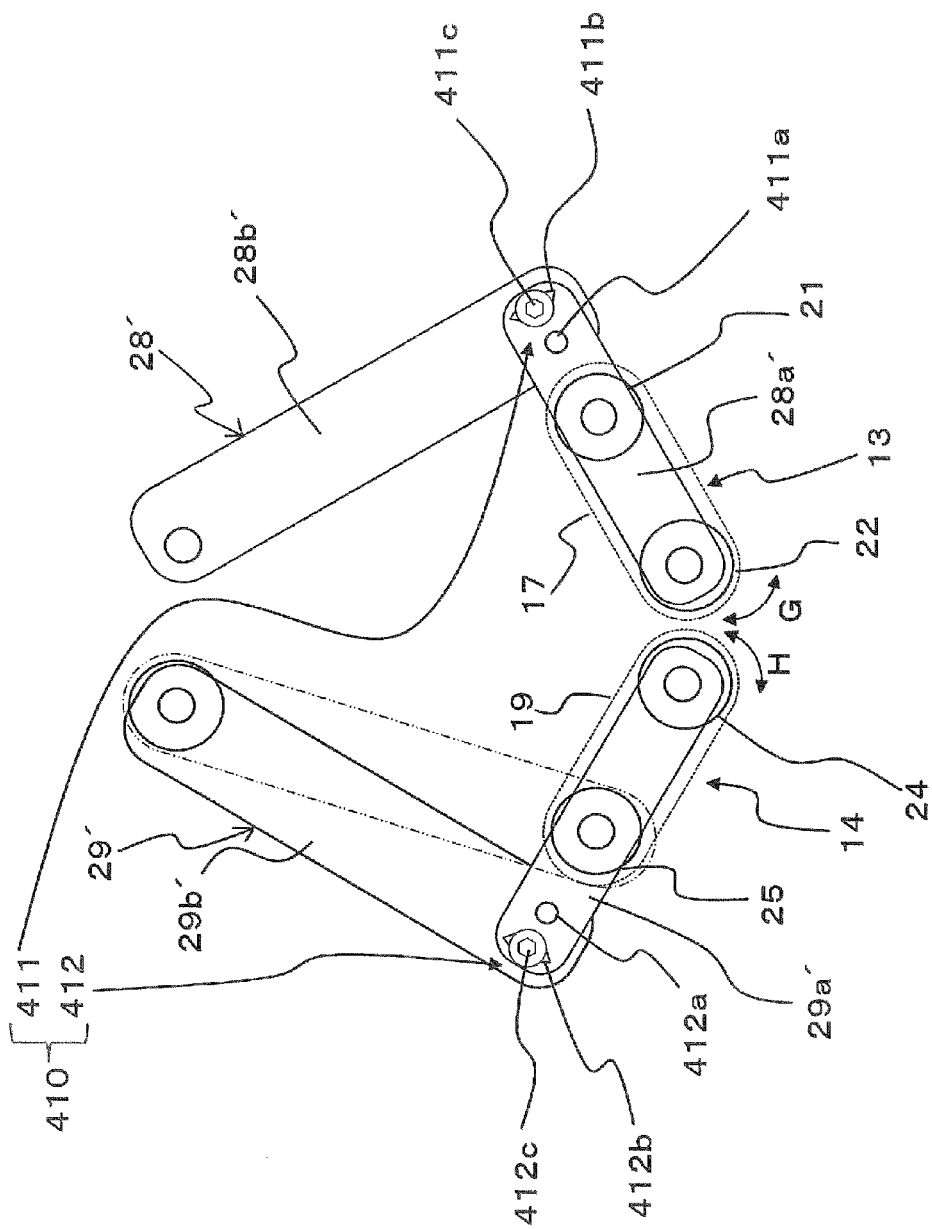
FIG. 14 is a diagram of the main parts of the removal head pertaining to a modification example of Embodiment 1 in the present invention.

FIG. 14 is a diagram of an angle variation component 410 that varies at least one of the angle of the movement face 17 and the angle of the movement face 19. As shown in FIG. 14, the angle variation component 410 has a movement-side angle variation component 411 that can vary the angle of the movement face 17, and a braking-side angle variation component 412 that can vary the angle of the movement face 19.

The arm 28' shown in FIG. 14 is different from the arm 28 shown in FIG. 4, and is configured such that it is separated into two members, namely, a first member 28a' and a second member 28b', and the angle formed by the first member 28a' and the second member 28b' can be adjusted. The first member 28a' and the second member 28b' are in the form of slender, thin plates, and the first member 28a' is attached rotatably around a rotational shaft 411a to the lower end of the second member 28b'. The first member 28a' is disposed along the movement path component 13, and is fixed to the movement path component 13.

The movement-side angle variation component 411 has the above-mentioned rotational shaft 411a, an angle adjustment slot 411b, and a bolt 411c. The angle adjustment slot 411b is formed on the opposite side from the movement path component 13, using the rotational shaft 411a of the first member 28a' as a reference. The angle adjustment slot 411b is formed in a substantially arced shape centered on the rotational shaft 411a. The bolt 411c is fitted into the angle adjustment slot 411b, and is fixed to the second member 28b'. When the bolt 411c is loose, the first member 28a' can be rotated up and down around the rotational shaft 411a (see the arrow G). The first member 28a' can be fixed at the desired angle with respect to the second member 28b' by tightening the bolt 411c after adjusting to the desired angle. This allows the movement face 17 linked to the first member 28a' to be fixed at the desired angle as well.

The arm 29' is similar in that it is different from the arm 29 shown in FIG. 4, and is configured such that it is separated into two members, namely, a first member 29a' and a second member 29b', and the angle formed by the first member 29a' and the second member 29b' can be adjusted. The first member 29a' and the second member 29b' are also in the form of slender, thin plates, and the first member 29a' is attached rotatably around a rotational shaft 412a to the lower end of the second member 29b'. The first member 29a' is disposed along the first braking component 14, and is fixed to the first braking component 14.

The braking-side angle variation component 412 has the above-mentioned rotational shaft 412a, an angle adjustment slot 412b, and a bolt 412c. The angle adjustment slot 412b is formed on the opposite side from the first braking component 14, using the rotational shaft 412a of the first member 29a' as a reference. The angle adjustment slot 412b is formed in a substantially arced shape centered on the rotational shaft 412a. The bolt 412c is fitted into the angle adjustment slot 412b, and is fixed to the second member 29b'. When the bolt 412c is loose, the first member 29a' can be rotated up and down around the rotational shaft 412a (see the arrow H). The first member 29a' can be fixed at the desired angle with respect to the second member 29b' by tightening the bolt 412c after adjusting to the desired angle. This allows the movement face 19 linked to the first member 29a' to be fixed at the desired angle as well.

Figure 15:
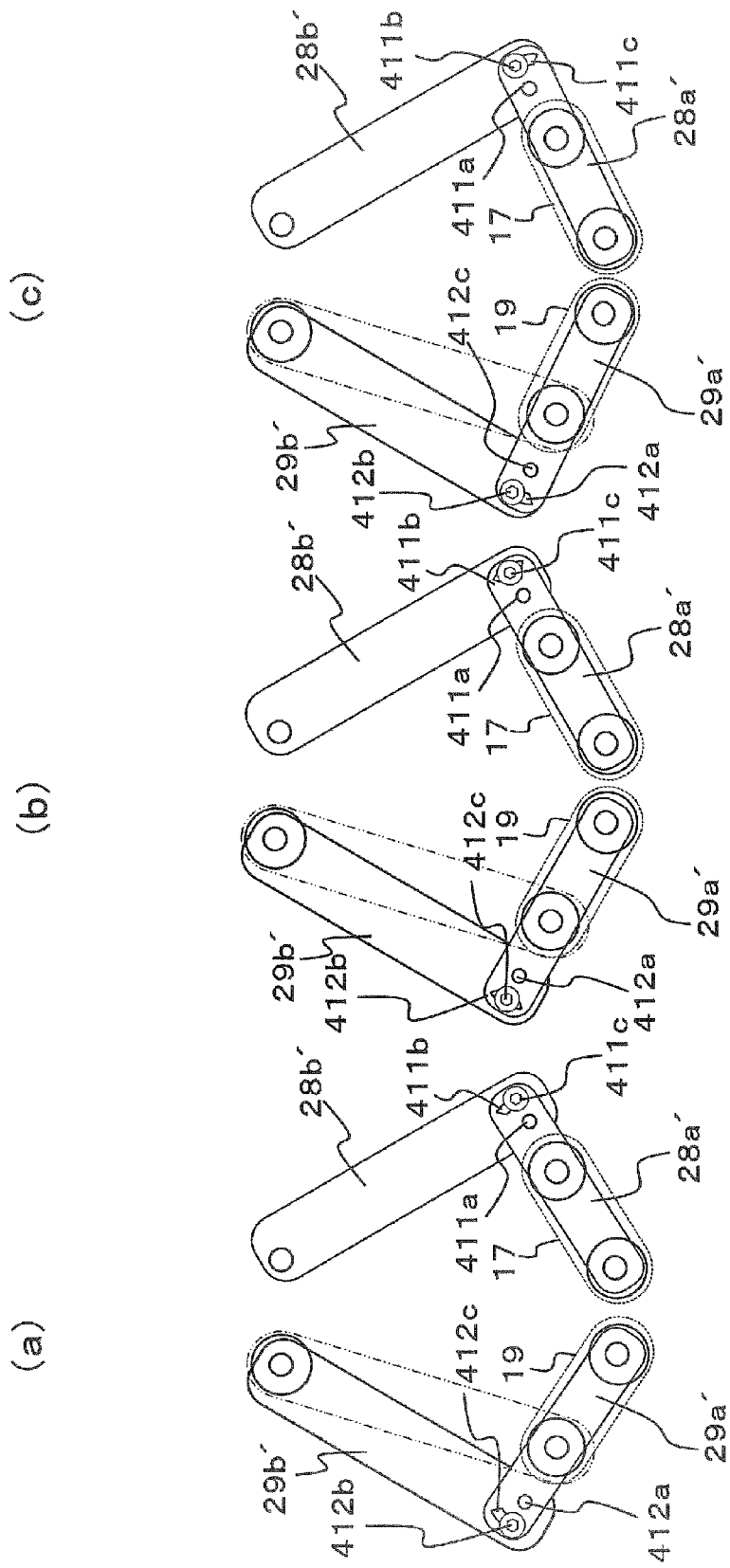
FIGS. 15a to 15c are diagrams illustrating states in which the angle of the movement face of the removal head shown in FIG. 14 has been changed.

FIGS. 15a to 15c show the state when the angles of the movement face 17 and the movement face 19 have been varied. FIG. 15b is the same as the state in FIG. 14. In FIG. 15a, the bolt 411c is located at the lower end of the angle adjustment slot 411b, the movement face 17 is at its greatest inclination, and the angle is acute. The bolt 412c is also located at the lower end of the angle adjustment slot 412b, the movement face 19 is at its greatest inclination, and the angle is acute.

In FIG. 15c, the bolt 411c is located at the upper end of the angle adjustment slot 411b, the movement face 17 is at its least inclination, and the angle is shallow. The bolt 412c is also located at the upper end of the angle adjustment slot 412b, the movement face 19 is at its least inclination, and the angle is shallow. FIG. 15b shows a state that is in between those in FIGS. 15a and 15c.

With this configuration, a pharmaceutical container 9 whose movement has been stopped by the first braking component 14 can be more reliably brought into contact with the contact component 18 of the movement face 17 according to the shape of the pharmaceutical container 9, and the pharmaceutical container 9 can be rotated more smoothly.

Furthermore, this configuration is sufficient to stop the movement of the pharmaceutical container 9, taking into account the energy produced as the pharmaceutical container 9 rolls down from the pharmaceutical container holding cassette 4, and the movement of the pharmaceutical container 9 can be more reliably stopped.

(A-2)

Figure 16:
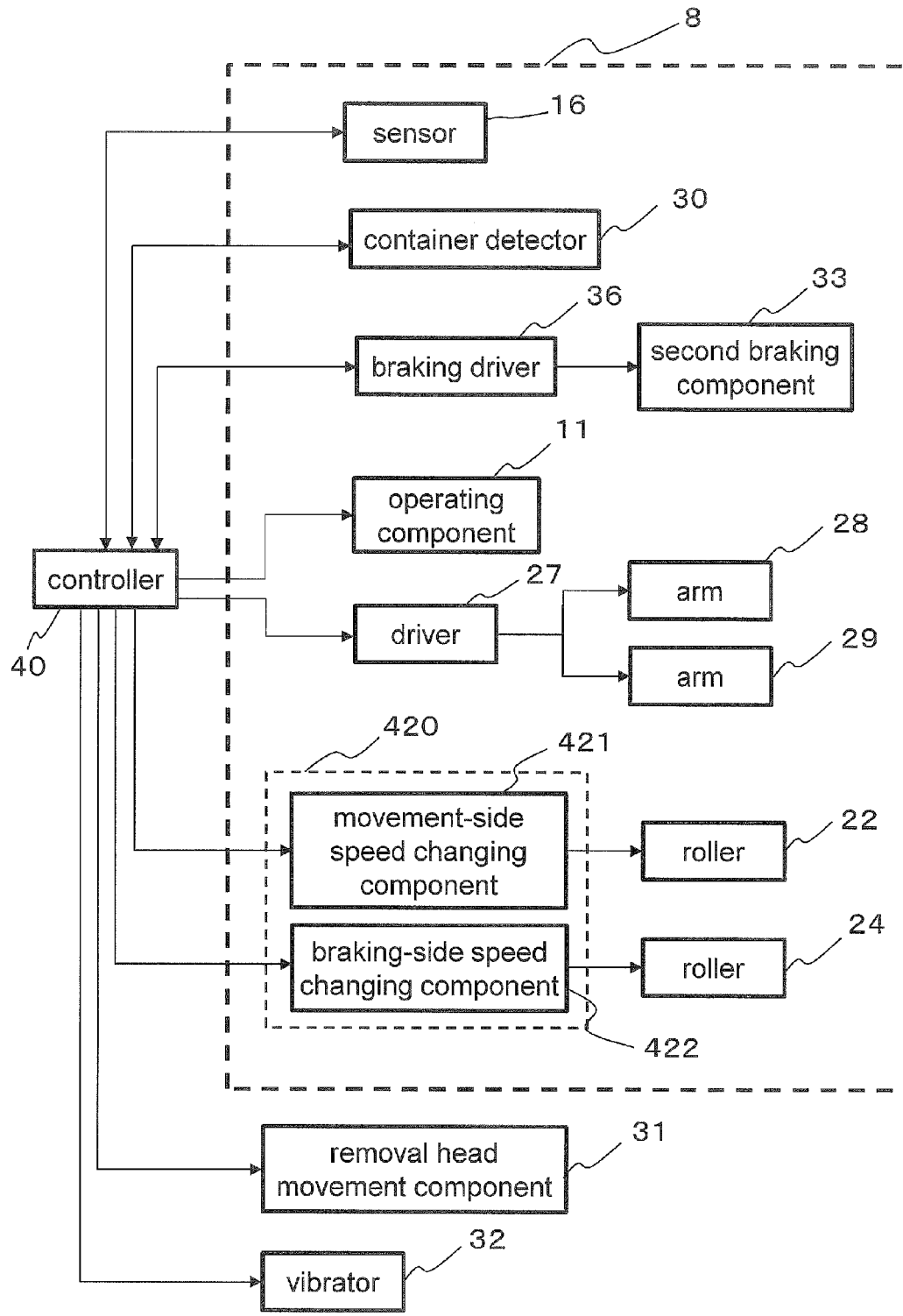
FIG. 16 is a schematic view of the control blocks of the pharmaceutical dispensing apparatus pertaining to a modification example of Embodiment 1 in the present invention.

Also, with the removal head 8 in the above embodiment, the speeds of the movement face 17 and the movement face 19 are each constant, but the configuration can be such that at least one of the movement speed of the movement face 17 and the movement speed of the movement face 19 can be varied according to the type of pharmaceutical container 9. For example, as shown in the block diagram of FIG. 16, a speed changing component 420 may be provided. The speed changing component 420 has a movement-side speed changing component 421 that changes the speed of the movement face 17 by changing the rotational speed of the roller 22, and a braking-side speed changing component 422 that changes the speed of the movement face 19 by changing the rotational speed of the roller 24. This configuration is sufficient to stop the movement of the pharmaceutical container 9, taking into account the energy produced as the pharmaceutical container 9 rolls down from the pharmaceutical container holding cassette 4, and the movement of the pharmaceutical container 9 can be more reliably stopped.

(A-3)

Also, at least one of the contact component 18 and the contact component 20 may be an elastic body.

Also, at least one of the contact component 18 and the contact component 20 may be configured such that the surface thereof is textured.

The result of this is that a pharmaceutical container 9 whose movement has been stopped by the first braking component 14 can be more reliably brought into contact with at least one of the contact component 18 and the contact component 20 according to the shape of the pharmaceutical container 9, and the pharmaceutical container 9 can be rotated more smoothly.

(B)

In the above embodiment, the sensor 16 read only the identification label 15 on the pharmaceutical container 9, but may also read other identification labels in addition to reading the identification label 15.

For instance, the configuration may be such that the pharmaceutical container holding cassette 4 has an identification label 35 (an example of a second identification label), and this identification label 35 (see FIG. 4) is also read by the sensor 16.

Figure 17:
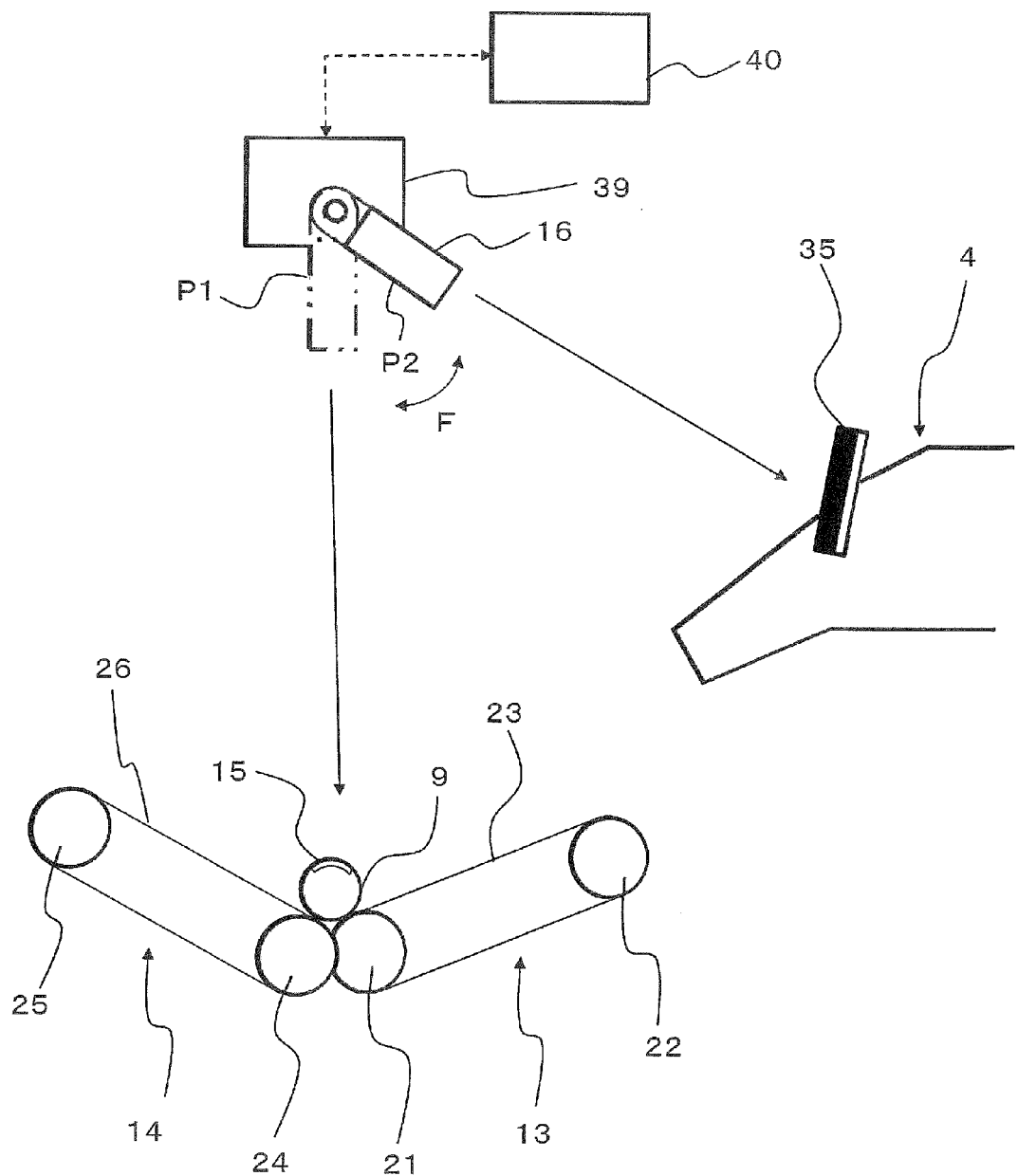
FIG. 17 is a schematic view of the sensor of the removal head pertaining to a modification example of Embodiment 1 in the present invention.

FIG. 17 is a schematic diagram of a configuration that allows the sensor 16 to read both the identification label 15 and the identification label 35.

As shown in FIG. 17, the sensor 16 is configured such that a pivot mechanism 39 allows it to move to a position P1 where the identification label 15 on the pharmaceutical container 9 is read, and to a position P2 where the identification label 35 on the pharmaceutical container holding cassette 4 is read. Specifically, the detection direction of the sensor 16 is switched by the pivot mechanism 39. In FIG. 17, the sensor 16 at the position P1 is indicated by a two-dot chain line, and the sensor 16 at the position P2 is indicated by a solid line. With the configuration shown in FIG. 17, the pivot mechanism 39 is constituted by a motor or the like, and the sensor 16 is configured to be rotatable (see the arrow F). Also, the pivot mechanism 39 is connected to the controller 40, and the orientation of the sensor 16 is controlled by the controller 40.

Doing this allows the pharmaceutical container 9 and the pharmaceutical container holding cassette 4 to be identified by a single sensor 16, so the resulting apparatus can be configured more rationally, with smaller size, lighter weight, and so on.

(C)

Figure 18:
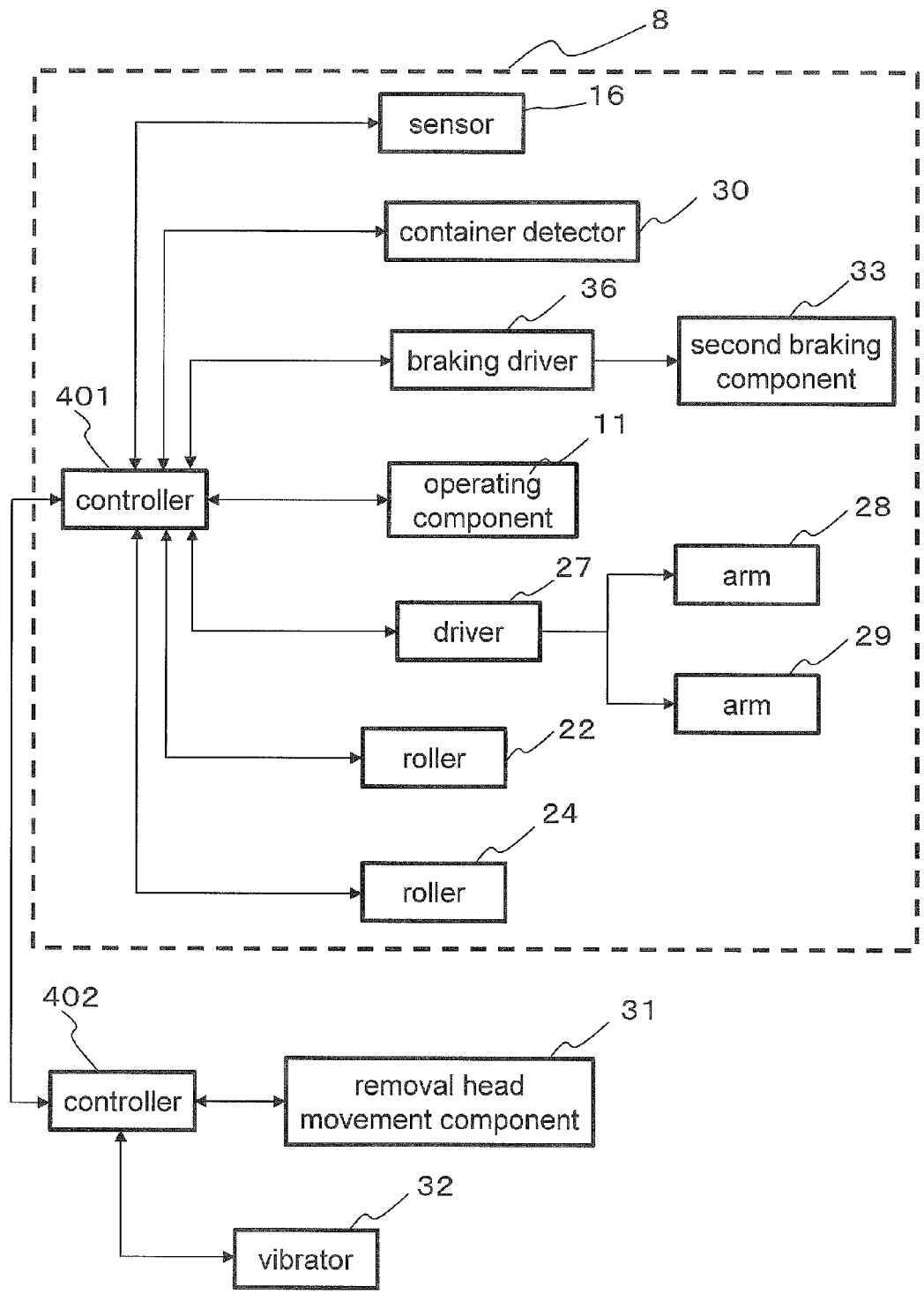
FIG. 18 is a schematic view of the control blocks of the pharmaceutical dispensing apparatus pertaining to a modification example of Embodiment 1 in the present invention.

With the pharmaceutical dispensing apparatus in the above embodiment, the roller 22, the roller 24, the driver 27, the operating component 11, the braking driver 36, the container detector 30, and the sensor 16 provided to the removal head 8 are controlled by the controller 40, which is provided separately from the removal head 8, but as shown in FIG. 18, the removal head 8 may have a controller 401 that controls the roller 22, the roller 24, the driver 27, the operating component 11, the braking driver 36, the container detector 30, and the sensor 16. In this case, the pharmaceutical dispensing apparatus also comprises a controller 402 that is provided separately from the removal head 8 and controls the removal head movement component 31, the vibrator 32, and so on. The controller 401 of the removal head 8 sends and receives signals to and from the controller 402, while controlling the roller 22, the roller 24, the driver 27, the operating component 11, the braking driver 36, the container detector 30, and the sensor 16.

(D)

Furthermore, in this embodiment, a configuration is described in which the vibrator 32 is provided to the removal head movement component 31 that moves the removal head 8, this vibrator 32 is vibrated, and the entire removal head 8 is vibrated, but this is not the only option.

The configuration may be such that a vibrator is provided so as to vibrate at least one of the movement path component 13 and the first braking component 14. That is, the removal head 8 may be configured, for example, such that a vibrator is provided to at least one of the movement path component 13 and the first braking component 14. In this case, as shown in FIG. 18, when the removal head 8 has the controller 401, the vibrator attached to the movement path component 13 or the first braking component 14 may be controlled by the controller 401.

(E)

Figure 19:
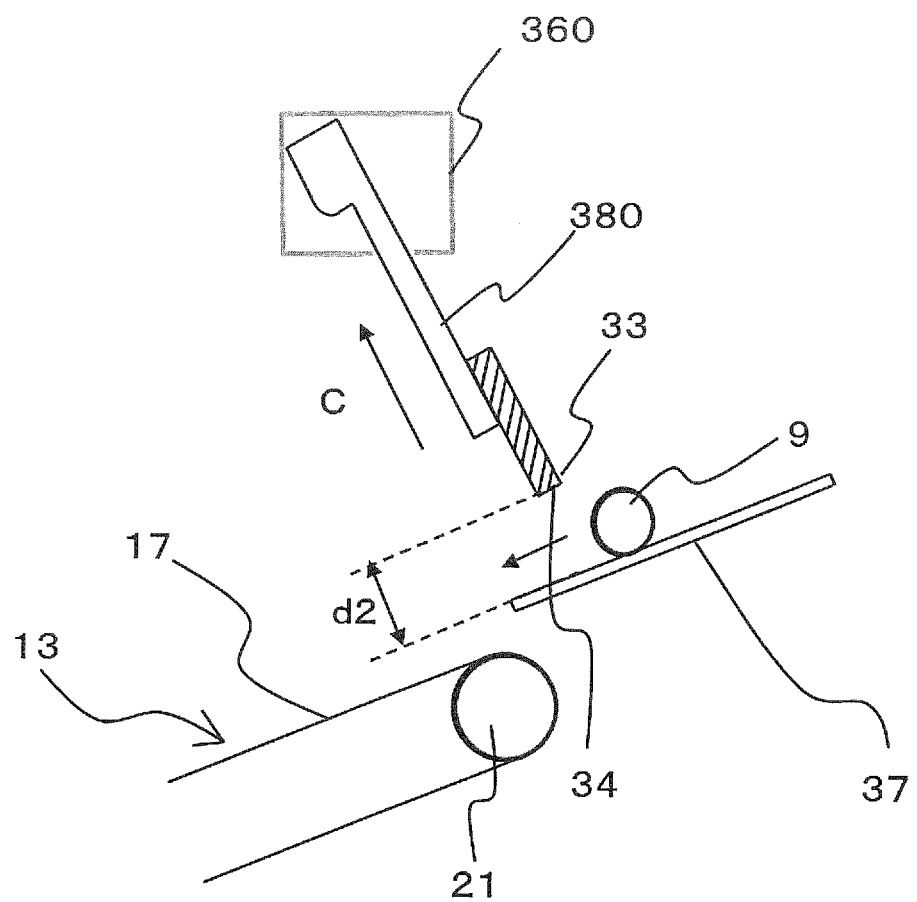
FIG. 19 is a schematic view of the area near the second braking component of the removal head pertaining to a modification example of Embodiment 1 in the present invention.

In the above embodiment, as shown in FIGS. 9A and 9B, the second braking component 33 was configured so as to rotate, but the second braking component 33 is not limited to a configuration in which it rotates, and may be configured so as to move in the lengthwise direction of the second braking component 33. Specifically, as shown in FIG. 19, a braking driver 360 may move a linking component 380 upward at an angle (see the arrow C), so that the end 34 of the second braking component 33 moves away from the area near the guide path 37. In this case, the height d2 by which the end 34 of the second braking component 33 moves away from the guide path 37 should be greater than the diameter of the pharmaceutical container 9.

Also, in the above embodiment, the second braking component 33 is provided near the upper face of the guide path 37, but may instead be provided near the movement face 17 of the movement path component 13, and may temporarily stop the pharmaceutical container 9 on the movement face 17.

(F)

In the above embodiment, the second braking component 33 is provided to temporarily stop the movement of the pharmaceutical container 9, and the movement speed of the pharmaceutical container 9 is reduced as it reaches the contact component 20 of the first braking component 14, but this effect can also be achieved without providing a driver to the second braking component 33.

Specifically, the elasticity of the second braking component 33 should be suitably set on the basis of the movement energy of the pharmaceutical container 9 as it rolls down from the pharmaceutical container holding cassette 4. That is, the elasticity may be set so that the moving pharmaceutical container 9 hits the second braking component 33, the movement speed of the pharmaceutical container 9 is reduced by the elasticity of the second braking component 33 itself, and then the pharmaceutical container 9 passes through the second braking component 33 without coming to a complete stop.

The pharmaceutical dispensing unit, the pharmaceutical dispensing apparatus comprising this unit, and the method for controlling a pharmaceutical dispensing apparatus of the present invention improve performance in the reading of an identification label on a pharmaceutical container, and as a result reliability can be enhanced. Therefore, it is fully anticipated that the present invention will find use as a pharmaceutical dispensing unit utilized to improve efficiency in hospital work, and as a pharmaceutical dispensing apparatus equipped with this unit.

REFERENCE SIGNS LIST 1 main cabinet
2 front door
3 cassette mounting slot
4 pharmaceutical container holding cassette (an example of a cassette)
5 tray
6 storage compartment
7 storage compartment
8 removal head (an example of a pharmaceutical dispensing unit)
9 pharmaceutical container
10 removal lever
11 operating component
12 holding pocket (an example of a holding component)
13 movement path component
13a end
14 first braking component (an example of a first braking component)
15 identification label
16 sensor
17 movement face (an example of a first movement face)
18 contact component (an example of a first contact component)
19 movement face (an example of a second movement face)
20 contact component (an example of a second contact component)
21 roller (an example of a first roller)
22 roller (an example of a second roller)
23 first belt
23A end
24 roller (an example of a third roller)
25 roller (an example of a fourth roller)
26 second belt
26A end
27 driver (an example of a driver)
28 arm (an example of a first arm)
28a first member
28b second member
28s rotational shaft
29 arm (an example of a second arm)

29a first member
29b second member
29s rotational shaft
30 container detector
30a light projector
30b light receiver
31 removal head movement component (an example of a movement component)
32 vibrator
33 second braking component (an example of a second braking component)
34 end
35 identification label (an example of a second identification label)
36 braking driver
37 guide path
38 linking component
38a shaft
39 pivot mechanism
40 controller
360 braking driver
380 linking component
401 controller
402 controller
410 angle variation component
411 movement-side angle variation component
412 braking-side angle variation component
420 speed changing component
421 movement-side speed changing component
422 braking-side speed changing component

The invention claimed is:

1. A pharmaceutical dispensing unit, comprising:
a movement path component that moves a substantially cylindrical pharmaceutical container that has a first identification label and has been taken out of a cassette in which the pharmaceutical container is housed;
a first braking component that is provided to the end of the movement path component and that stops the pharmaceutical container that has come along the movement path component at a specific location; and
a sensor that reads the first identification label on the pharmaceutical container whose movement has been stopped at the specific location by the first braking component,
wherein the movement path component has a first movement face that moves in a rotational direction along a movement path of the pharmaceutical container,
the first movement face is an inclined surface and has a first contact component that comes into contact with the pharmaceutical container, the pharmaceutical container rolling down the inclined surface of the first movement face and moving in a rotational direction while in contact with first contact component of the first movement face, and
the first movement face moves in the rotational direction which in an opposite direction from the rotational direction of the pharmaceutical container while the pharmaceutical container moves along the movement path.

2. The pharmaceutical dispensing unit according to claim 1, wherein the first braking component has a second movement face that moves in a rotational direction that is an opposite direction from the movement direction of the pharmaceutical container, and the second movement face has a second contact component that comes into contact with the pharmaceutical container.

3. The pharmaceutical dispensing unit according to claim 2, further comprising an angle changing component that changes at least one of an angle of the first movement face and an angle of the second movement face according to an identification of the pharmaceutical container.

4. The pharmaceutical dispensing unit according to claim 2, further comprising a speed changing component that changes at least one of a movement speed of the first movement face and a movement speed of the second movement face according to an identification of the pharmaceutical container.

5. The pharmaceutical dispensing unit according to claim 2, wherein the first braking component has:
a third roller that is provided to the rear of the first movement face in the movement direction of the pharmaceutical container;
a fourth roller that is provided at a location to the rear of the third roller and above the third roller; and
a second belt that goes between the third roller and the fourth roller, and
the second movement face is formed by driving at least one of the third roller and the fourth roller so that the second belt is rotated between the third roller and the fourth roller.

6. The pharmaceutical dispensing unit according to claim 2, wherein the movement path component has:
a first roller that is provided between the cassette and the first braking component, closer to the cassette;
a second roller that is provided at a location lower than the first roller and closer to the first braking component than the first roller; and
a first belt that goes between the first roller and the second roller,
the first movement face is formed by driving at least one of the first roller and the second roller so that the first belt is rotated between the first roller and the second roller,
the first braking component has:
a third roller that is provided to the rear of the first movement face in the movement direction of the pharmaceutical container;
a fourth roller that is provided at a location to the rear of the third roller and above the third roller; and
a second belt that goes between the third roller and the fourth roller,
the second movement face is formed by driving at least one of the third roller and the fourth roller so that the second belt is rotated between the third roller and the fourth roller,
a plurality of the first belts are provided, and these first belts go between the first roller and the second roller at a specific spacing, and
a plurality of the second belts are provided, and these second belts go between the third roller and the fourth roller at a specific spacing.

7. The pharmaceutical dispensing unit according to claim 6,
wherein the ends of the first belts are placed within the specific spacing of the second belts;
the ends of the second belts are placed within the specific spacing of the first belts, and
the ends of the first belts and the ends of the second belts intersect when viewed from a direction parallel to both the first movement face and the second movement face.

8. The pharmaceutical dispensing unit according to claim 1, wherein the movement path component has:
- a first roller that is provided between the cassette and the first braking component, closer to the cassette;
- a second roller that is provided at a location lower than the first roller and closer to the first braking component than the first roller; and
- a first belt that goes between the first roller and the second roller, and
- the first movement face is formed by driving at least one of the first roller and the second roller so that the first belt is rotated between the first roller and the second roller.

9. The pharmaceutical dispensing unit according to claim 1, further comprising:
- a driver that produces a specific gap between the first braking component and the end of the movement path component; and
- a holding compartment that is provided under the first braking component to house the pharmaceutical container that has dropped through the specific gap produced by the driver.

10. The pharmaceutical dispensing unit according to claim 1, further comprising:
- a driver that moves at least one of the movement path component and the first braking component and opens and closes a space between the movement path component and the first braking component, thereby dropping the pharmaceutical container;
- a container detector that detects the presence or absence of the pharmaceutical container at the specific location; and
- a controller that controls the driver according to a detection result of the container detector.

11. The pharmaceutical dispensing unit according to claim 10, wherein the controller puts the space between the movement path component and the first braking component in an open state, and puts the space between the movement path component and the first braking component in a closed state when the container detector has detected that there is no pharmaceutical container.

12. The pharmaceutical dispensing unit according to claim 10, further comprising a vibrator that vibrates at least one of the movement path component and the first braking component,
wherein the controller puts the space between the movement path component and the first braking component in an open state, and drives the vibrator when the container detector has detected that there is a pharmaceutical container.

13. The pharmaceutical dispensing unit according to claim 12, wherein the controller puts the space between the movement path component and the first braking component in a closed state when the container detector has detected that there is no pharmaceutical container after the vibrator has been driven.

14. A pharmaceutical dispensing apparatus equipped with the pharmaceutical dispensing unit according to claim 1.

15. A pharmaceutical dispensing apparatus, comprising:
the pharmaceutical dispensing unit according to claim 1, further having a driver that moves at least one of the movement path component and the first braking component and opens or closes a space between the movement path component and the first braking component, thereby dropping the pharmaceutical container, and a container detector that detects the presence or absence of the pharmaceutical container at the specific location; and
a controller that controls the driver according to a detection result of the container detector.

16. The pharmaceutical dispensing apparatus according to claim 15, further comprising a vibrator that vibrates at least one of the movement path component and the first braking component,
wherein the controller puts the space between the movement path component and the first braking component in an open state, and drives the vibrator when the container detector has detected that there is a pharmaceutical container.

17. The pharmaceutical dispensing apparatus according to claim 16, further comprising a movement component that moves the pharmaceutical dispensing unit,
wherein the vibrator is provided to the movement component, and vibrates the pharmaceutical dispensing unit.

18. A method for controlling a pharmaceutical dispensing apparatus equipped with a pharmaceutical dispensing unit having:
- a movement path component for moving a substantially cylindrical pharmaceutical container that has a first identification label indicating pharmaceutical information and that has been taken out of a cassette in which the pharmaceutical container is housed; and
- a first braking component that is provided to the end of the movement path component and that stops the pharmaceutical container that has come along the movement path component at a specific location,
- the movement path component having a first movement face that moves in a rotational direction along the movement path of the pharmaceutical container, and the first movement face having an inclined surface and a first contact component that comes into contact with the pharmaceutical container, the pharmaceutical container rolling down the inclined surface of the first movement face and moving in a rotational direction while in contact with first contact component of the first movement face, and
- the first movement face moves in the rotational direction which in an opposite direction from the rotational direction of the pharmaceutical container while the pharmaceutical container moves along the movement path, the method comprising:
- a removal step of removing the pharmaceutical container to the pharmaceutical dispensing unit side;
- a movement step of moving the first movement face in a rotational direction;
- a reading step of reading the first identification label of the pharmaceutical container whose movement after removal has been stopped at the specific location by the first braking component;
- a first drive step of moving at least one of the movement path component and the first braking component and opening a space between the movement path component and the first braking component;
- a container detection step of detecting the presence or absence of the pharmaceutical container at the specific location after the first drive step; and
- a second drive step of closing the space between the movement path component and the first braking component if it is detected in the container detection step that there is no pharmaceutical container, wherein, in the reading step, the reading of the first identification label is performed while the pharmaceutical container is rotated at the specific location by the movement of the first movement face.

19. The method for controlling a pharmaceutical dispensing apparatus according to claim 18, further comprising a vibration step of vibrating at least one of the movement path component and the first braking component if it is detected in the container detection step that there is a pharmaceutical container.

* * * * *